(12) United States Patent
Ryu et al.

(10) Patent No.: US 7,030,090 B2
(45) Date of Patent: Apr. 18, 2006

(54) IMMUNE-MODULATING PEPTIDE

(75) Inventors: Sung-Ho Ryu, Pohang (KR); Pann-Ghill Suh, Pohang (KR); Yoe-Sik Bae, Pohang (KR); Ji-Young Song, Pohang (KR)

(73) Assignees: Posco, Pohang-Shi (KR); Postech Foundation, Pohang (KR)

( * ) Notice: Subject to any disclaimer, the term of this patent is extended or adjusted under 35 U.S.C. 154(b) by 98 days.

(21) Appl. No.: 10/353,419

(22) Filed: Jan. 29, 2003

(65) Prior Publication Data

US 2003/0224987 A1   Dec. 4, 2003

Related U.S. Application Data

(60) Provisional application No. 60/352,930, filed on Jan. 29, 2002.

(51) Int. Cl.
*A61K 38/08* (2006.01)
*C07K 7/06* (2006.01)

(52) U.S. Cl. .................................... 514/17; 530/329
(58) Field of Classification Search ............... 514/17; 530/329
See application file for complete search history.

(56) References Cited

U.S. PATENT DOCUMENTS 6,777,195 B1 *  8/2004  Kozhemyakin et al. ..... 435/7.24

OTHER PUBLICATIONS

Le et al., (2000) "Novel pathophysiological role of classical chemotactic peptide receptors and their communications with chemokine receptors", Immunol. Rev., vol. 177: pps. 185-194.
Le et al., (2001) "Pleiotropic roles of formyl peptide receptors", Cytokine and Growth Factor Rev. 12: pps. 91-105.
White et al., (1998) "Identification of a potent selective non-peptide CXCR2 Antagonist that inhibits interleukin-8-induced neutrophil migration", J. Biol. Chem. 273: pps. 10095-10096.
Zagorski et al., (1997), Inhibition of acute peritoneal inflammation in rats by a cytokine-induced neutrophil chemoattractant receptor antagonist, J. Immunol. 159: pps. 1059-1062.
Prossnitz et al., (1997) "The N-formyl peptide receptor: A model for the study of chemoattractant receptor structure and function", Pharmacol. Ther. 74: pps. 73-102.
Su et al., (1999) "T20/DP178, an ectodomain peptide of human immunodeficiency virus type 1 gp41, is an activator of human phagocyte N-formyl peptide receptor", Blood 93: pps. 3885-3892.
Walther et al., (2000) "A novel ligand of the formyl peptide receptor: Annexin I regulates neutrophil extravasation by interacting with the FPR", Mol. Cell. 5: pps. 831-840.
Baek., (1996) "identification of the peptides that stimulate the phosphoinositide hydrolysis in lymphocyte cell lines from peptide libraries", J. Biol. Chem. 270: pps. 8170-8175.
Seo et al., (1997) "A peptide with unique receptor specificity", J. Immunol. 158: pps. 1895-1901.
Bae et al., (1999) "Trp-Lys-Tyr-Met-Val-D-Met stimulates superoxide generation and killing of *Staphylococcus aureus* via phospholipase D activation in human monocytes", J. Leukoc. Biol. 65: pps. 241-248.
Bae et al., (1999) "Trp-Lys-Tyr-Met-Val-D-Met is a chemoattractant for human phagocytic cells", J. Leukoc. Biol. 66: pps. 915-922.
Le et al., (1999) "Utilization of two seven-transmembrane, G protein-coupled receptors, formyl peptide receptor-like 1 and formyl peptide receptor, by the synthetic hexapeptide WKYMVm for human Phagocyte activation", J. Immunol. 163: pps. 6777-6784.
He et al., (2000) "The synthetic peptide Trp-Lys-Tyr-Met-Val-D-Met is a potent chemotactic agonist for mouse formyl peptide receptor", J. Immunol. 165: pps. 4598-4605.

(Continued)

*Primary Examiner*—Jeffrey Edwin Russel
(74) *Attorney, Agent, or Firm*—Baker Botts L.L.P.

(57) ABSTRACT

Disclosed are peptides having SEQ ID NOs: 1 to 24 that induce superoxide generation by human monocytes or neutrophils; that induce an intracellular calcium increase by human peripheral blood monocytes or neutrophils; binds to formyl peptide receptor or formyl peptide receptor-like 1; that induce chemotactic migration of human monocytes or neutrophils in vitro; that induce degranulation in formyl peptide receptor expressing cells or formyl peptide receptor-like 1 expressing cells; that stimulate extracellular signal regulated protein kinase phosphorylation via activation of formyl peptide receptor or formyl peptide receptor-like 1; or that stimulate Akt phosphorylation via activation of formyl peptide receptor or formyl peptide receptor-like 1.

26 Claims, 8 Drawing Sheets

OTHER PUBLICATIONS

Bae et al., (2001) "Identification of novel chemoattractant peptides from human leukocytes", Blood 97: pps. 2854-2862.

Grynkiewicz et al., (1986) "A new generation of $Ca^{2+}$ Indicators with greatly improved fluorescence properties", J. Biol. Chem. 260: pps. 3440-3450.

Hu et al., (2001) "Synthetic peptide MMK-1 is a highly specific chemotactic agaonist for leukocyte FPRL1", J. Leukoc. Biol. 70: pps. 155-161.

King et al., (1971) "Polypeptides of the tail fibres of bacteriophage T4", J. Mol. Biol. 65: pps. 465-477.

Hirababu et al., (1999) "Chemoattractant receptors activate distinct pathways for chemotaxis and secretion", J. Biol. Chem. 274: pps. 37087-37092.

Franke et al., (1995) "The protein kinase encoded by the Akt proto-oncogene is a target of the PDGF-activated phosphatidylinositol 3-kinase", Cell. 81: pps. 727-736.

Jin et al., (1997) "Inosine binds to $A_3$ Adenosine receptors and stimulates mast cell degranulation", J. Clin. Invest. 100: pps. 2849-2857.

Thomas et al., (2000) "Agonist-induced phosphotylation of the angiotensin II ($AT_{1A}$) receptor requires generation of a conformation that is distinct from the inositol phosphate-signaling state", J. Biol. Chem. 275: pps. 2893-2900.

Palanche et al., (2001) "The neurokinin A receptor activates calcium and cAMP responses distinct conformational states", J. Biol. Chem. 276: pps. 34853-34861.

Prossnitz et al., (1993) "The role of the third intracellular loop of the neutrophil N-formyl peptide receptor in G protein coupling", Biochem. J. 294: pps. 581-587.

Miettinen et al., (1999) "Identification of putative sites of interaction between the human formyl peptide receptor and G protein", J. Biol. Chem. 274: pps. 27934-27942.

Li et al., "The Synthetic Peptide WKYMVm Attenuates the Function of the Chemokine Receptors CCR5 and CXCR4 Through Activation of Formyl Peptide Receptor-Like 1," BLOOD, vol. 97, No. 10, May 15, 2001, pp 2941-2947.

Christophe et al., "The Synthetic Peptide Trp-Lys-Tyr-Met-Val-Met-$NH_2$ Specifically Activates Neutrophils through FPRL1/Lipoxin $A_4$ Receptors and Is an Agonist for the Orphan Monocyte-expressed Chemoattractant Receptor FPRL2," The Journal of Biological Chemistry, vol. 276, No. 24, Jun. 15, 2001, pp. 21585-21593.

He et al., "The Synthetic Peptide Trp-Lys-Tyr-Met-Val-D-Met Is a Potent Chemotactic Agonist for Mouse Formyl Peptide Receptor," The Journal of Immunology, 2000, 165: pp. 4598-4605.

Bae et al., "Independent Functioning of Cytosolic Phospholipase $A_2$ and Phospholipase $D_1$ in Trp-Lys-Tyr-Met-Val-D-Met-Induced Superoxide Generation in Human Monocytes," The Journal of Immunology, 2000, 164: pp. 4089-4096.

Baek et al., "Trp-Lys-Tyr-Met-Val-Met Activates Mitogen-Activated Protein Kinase Via A PI-3 Kinase-Mediated Pathway Independent of PKC," Life Sciences, vol. 65, No. 17, 1999, pp. 1845-1856; and.

Seo et al., "Distribution of the Receptor for a Novel Peptide Stimulating Phosphoinositide Hydrolysis in Human Leukocytes," Clinical Biochemistry, vol. 31, No. 3, 1998, pp. 137-141.

* cited by examiner

SEQUENCE LISTING

<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES

```
<222> LOCATION: 6
<223> OTHER INFORMATION: D-Met

<400> SEQUENCE: 1

Trp Lys Gly Met Val Met
1               5

<210> SEQ ID NO 2
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 2

Trp Lys Tyr Met Gly Met
1               5

<210> SEQ ID NO 3
<211> LENGTH: 6
<212> TYPE: PRT
<213> ORGANISM: Artificial Sequence
<220> FEATURE:
<223> OTHER INFORMATION: Immune-modulating peptide

<400> SEQUENCE: 3

Trp Lys Tyr Met Val Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 4

Trp Arg Tyr Met Val Met
1               5

<210> SEQ ID NO 5
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 5

Trp Glu Tyr Met Val Met
1               5

<210> SEQ ID NO 6
<211> LENGTH: 6
<212> TYPE: PRT
<213> ORGANISM: Artificial Sequence
<220> FEATURE:
<223> OTHER INFORMATION: Immune-modulating peptide
```

```
<220> FEATURE:
<221> NAME/KEY: MOD_RES
<222> LOCATION: 6
<223> OTHER INFORMATION: D-Met

<400> SEQUENCE: 6

Trp His Tyr Met Val Met
1               5

<210> SEQ ID NO 7
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 7

Trp Asp Tyr Met Val Met
1               5

<210> SEQ ID NO 8
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 8

Trp Lys His Met Val Met
1               5

<210> SEQ ID NO 9
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 9

Trp Lys Glu Met Val Met
1               5

<210> SEQ ID NO 10
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 10

Trp Lys Trp Met Val Met
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 11

Trp Lys Arg Met Val Met
 1               5

<210> SEQ ID NO 12
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 12

Trp Lys Asp Met Val Met
 1               5

<210> SEQ ID NO 13
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 13

Trp Lys Phe Met Val Met
 1               5

<210> SEQ ID NO 14
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met

<400> SEQUENCE: 14

Trp Lys Tyr Met Tyr Met
 1               5

<210> SEQ ID NO 15
<211> LENGTH: 6
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 6
<223> OTHER INFORMATION: D-Met
<220> FEATURE:
```

-continued

<221> NAME/KEY: VARIANT
<222> LOCATION: 5
<223> OTHER INFORMATION: Phenylalanine or Tryptophan

<400> SEQUENCE: 15

Trp Lys Tyr Met Xaa Met
 1 5

<210> SEQ ID NO 16
<211> LENGTH: 6
<212> TYPE: PRT
<213> ORGANISM: Artificial Sequence
<220> FEATURE:
<223> OTHER INFORMATION: Immune-modulating peptide

<400> SEQUENCE: 16

Trp Lys Tyr Met Val Glu
 1 5

<210> SEQ ID NO 17
<211> LENGTH: 6
<212> TYPE: PRT
<213> ORGANISM: Artificial Sequence
<220> FEATURE:
<223> OTHER INFORMATION: Immune-modulating peptide

<400> SEQUENCE: 17

Trp Lys Tyr Met Val Val
 1 5

<210> SEQ ID NO 18
<211> LENGTH: 6
<212> TYPE: PRT
<213> ORGANISM: Artificial Sequence
<220> FEATURE:
<223> OTHER INFORMATION: Immune-modulating peptide

<400> SEQUENCE: 18

Trp Lys Tyr Met Val Arg
 1 5

<210> SEQ ID NO 19
<211> LENGTH: 6
<212> TYPE: PRT
<213> ORGANISM: Artificial Sequence
<220> FEATURE:
<223> OTHER INFORMATION: Immune-modulating peptide

<400> SEQUENCE: 19

Trp Lys Tyr Met Val Trp
 1 5

<210> SEQ ID NO 20
<211> LENGTH: 5
<212> TYPE: PRT
<213> ORGANISM: Artificial Sequence
<220> FEATURE:
<223> OTHER INFORMATION: Immune-modulating peptide

<400> SEQUENCE: 20

Trp Lys Tyr Met Val
 1 5

<210> SEQ ID NO 21
<211> LENGTH: 5
<212> TYPE: PRT
<213> ORGANISM: Artificial Sequence -continued

```
<220> FEATURE:
<223> OTHER INFORMATION: Immune-modulating peptide
<220> FEATURE:
<221> NAME/KEY: MOD_RES
<222> LOCATION: 5
<223> OTHER INFORMATION: D-Met

<400> SEQUENCE: 21

Lys Tyr Met Val Met
 1               5

<210> SEQ ID NO 22
<211> LENGTH: 4
<212> TYPE: PRT
<213> ORGANISM: Artificial Sequence
<220> FEATURE:
<223> OTHER INFORMATION: Immune-modulating peptide

<400> SEQUENCE: 22

Lys Tyr Met Val
 1

<210> SEQ ID NO 23
<211> LENGTH: 4
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 4
<223> OTHER INFORMATION: D-Met

<400> SEQUENCE: 23

Tyr Met Val Met
 1

<210> SEQ ID NO 24
<211> LENGTH: 3
<212> TYPE: PRT
<213> ORGANISM: Artificial Sequence
<220> FEATURE:
<223> OTHER INFORMATION: Immune-modulating peptide
<220> FEATURE:
<221> NAME/KEY: MOD_RES
<222> LOCATION: 3
<223> OTHER INFORMATION: D-Met

<400> SEQUENCE: 24

Met Val Met
 1
```

US 7,030,090 B2

IMMUNE-MODULATING PEPTIDE

CROSS REFERENCE TO RELATED APPLICATIONS

This application claims the benefit under 35 U.S.C. §119 (e) of the U.S. Provisional Application Ser. No. 60/352,930, entitled "IMMUNE-MODULATING PEPTIDE", filed Jan. 29, 2002.

BACKGROUND OF THE INVENTION

The present invention relates to an immune-modulating peptide. The formyl peptide receptor family (formyl peptide receptor (FPR) and formyl peptide receptor-like 1 (FPRL1)) that is expressed in phagocytic cells such as neutrophils and monocytes plays an important role in host defense against pathogen infection. Le, Y., Li, B., Gong, W., Shen, W., Hu, J., Dunlop, N. M., Oppenheim, J. J., and Wang, J. M. (2000) Immunol Rev. 177, 185–194; Le, Y., Oppenheim, J. J., and Wang, J. M. (2001) Cytokine Growth Factor Rev. 12, 91–105. The receptors have been known to couple with pertussis toxin-sensitive Gi proteins. Activation of FPR induces dissociation of G$\beta\gamma$ subunits from G$\alpha$i subunits, and the $\beta\gamma$--subunits mediate the activation of phospholipase C$\beta$ or phosphoinositide 3-kinase Activation of these effect molecules induces complicated downstream signaling leading to diverse cellular responses such as chemotactic migration, degranulation, and superoxide generation.

Most full agonists induce a lot of complicated cellular signaling that evokes eventual complex immune responses. Among the immune responses, many of them are essentially required for the proper functioning of host cells to clear out invading pathogens, but some responses are unwanted side effects in immune responses. In the area of drug development, it has been a hot issue to reduce or remove the side effects of drug candidates. To obtain this objective, many research groups have tried to develop selective immune response modulators or selective antagonists for specific receptors via several approaches. White, J. R., Lee, J. M., Young, P. R., Hertzberg, R. P., Jurewicz, A. J., Chaikin, M. A., Widdowson, K., Foley, J. J., Martin, L. D., Griswold, D. E., and Sarau, H. M. (1998) J. Biol. Chem. 273, 10095–10098; Zagorski, J., and Wahl, S. M. (1997) J. Immunol. 159, 1059–1062.

A variety of agonists for FPR have been identified from endogenous sources or artificial synthesis. They include bacterial peptides (N-formyl-methionyl-leucyl-phenylalanine (fMLF)), HIV-envelope domains (T20 and T21), and host-derived agonists (Annexin I and A$\beta_{42}$). Prossnitz, E. R., and Ye, R. D. (1997) Pharmacol. Ther. 74, 73–102; Su, S. B., Gong, W. H., Gao, J. L., Shen, W. P., Grimm, M. C., Deng, X., Murphy, P. M., Oppenheim, J. J., and Wang, J. M. (1999) Blood 93, 3885–3892; Walther, A., Riehemann, K., and Gerke, V. (2000) Mol. Cell. 5, 831–840. Previously, the inventors of the present invention reported a synthetic peptide ligand, Trp-Lys-Tyr-Met-Val-D-Met-NH$_2$ (hereinafter, referred to as "WKYMVm") that stimulates leukocytic cells such as monocytes and neutrophils. Baek, S. H., Seo, J. K., Chae, C. B., Suh, P. G., and Ryu, S. H. (1996) J. Biol. Chem. 271, 8170–8175; Seo, J. K., Choi, S. Y., Kim, Y., Baek, S. H., Kim, K. T., Chae, C. B., Lambeth, J. D., Suh, P. G., and Ryu, S. H. (1997) J. Immunol. 158, 1895–1901; Bae, Y. S., Ju, S. A., Kim, J. Y., Seo, J. K., Back, S. H., Kwak, J. Y., Kim, B. S., Suh, P. G., and Ryu, S. H. (1999) J. Leukoc. Biol. 65, 241–248; Bae, Y. S., Kim, Y., Kim, Y., Kim, J. H., Suh, P. G., and Ryu, S. H. (1999) J. Leukoc. Biol. 66, 915–922. Le et al. demonstrated that WKYMVm binds to formyl peptide receptor (FPR) and formyl peptide receptor-like 1 (FPRL1). Le, Y., Gong, W., Li, B., Dunlop, N. M., Shen, W., Su, S. B., Ye, R. D., and Wang, J. M. (1999) J. Immunol. 163, 6777–6784. Since WKYMVm is a short peptide with a high affinity for a broad spectrum of receptors, it can be a useful material for the study of FPR- or FPRL1-mediated signaling. However, research to develop selective immuno-modulators or selective antagonists for specific receptors, as well as screening of molecular diversity, consists of small compounds and thus far has been very limited, and therefore there are continuing demands for identifying novel compounds.

SUMMARY OF THE INVENTION

It is a first object of the present invention to provide a novel immune-modulating peptide having an amino acid sequence selected from the group consisting of SEQ ID NO: 1 to SEQ ID NO: 24; or a substance derived from the peptide of which the amino acid sequence is selected from the group consisting of SEQ ID NO: 1 to SEQ ID NO: 24.

It is a second object to provide a pharmaceutical composition comprising a peptide having an amino acid sequence selected from the group consisting of SEQ ID NO: 1 to SEQ ID NO: 24; or a substance derived from the peptide of which the amino acid sequence is selected from the group consisting of SEQ ID NO: 1 to SEQ ID NO: 24.

It is a third object to provide a method of treating a condition accompanied or caused by modification of the number or activation states of leukocytes comprising administering to a host in need of such treatment a therapeutically effective amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24.

It is a fourth object to provide a method of increasing the number or raising the activation state of leukocytes in a host, comprising administering to a host in need of a greater number or higher activation state of leukocytes a therapeutically effective amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24.

It is a fifth object to provide a method of inducing an extracellular calcium increase in leukocytes in a patient in need of such treatment, the method comprising administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is a sixth object to provide a method of inducing superoxide generation by human monocytes or neutrophils in a patient in need of such treatment, the method comprising administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is a seventh object to provide a method of inducing chemotactic migration by human peripheral blood mononuclear cells in a patient in need of such treatment, the method comprising administering to said patient an amount of peptides having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is an eighth object to provide a method of inducing degranulation in formyl peptide receptor expressing cells or formyl peptide receptor-like 1 expressing cells in a patient in need of such treatment, the method comprising administering to said patient an amount of peptides having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is a ninth object to provide a method of competing peptides with WKYMVm for binding formyl peptide receptor or a formyl peptide receptor-like 1 in the formyl peptide receptor expressing cells or formyl peptide receptor-like 1 expressing cells, respectively, in a patient in need of such treatment, the method comprising administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is a tenth object to provide a method of stimulating extracellular signal regulated protein kinase in formyl peptide receptor expressing cells or formyl peptide receptor-like 1 expressing cells in a patient in need of such treatment, the method comprising administering to said patient an amount of peptides having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is an eleventh object to provide a method of stimulating Akt in formyl peptide receptor expressing cells or formyl peptide receptor-like 1 expressing cells in a patient in need of such treatment, the method comprising administering to said patient an amount of peptides having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

It is a twelfth object to provide an isolated nucleotide encoding peptides of amino acid sequences selected from the group consisting of SEQ ID NO: 1 to SEQ ID NO: 24.

It is a thirteenth object to provide a vector comprising an isolated nucleotide encoding peptides of amino acid sequences selected from the group consisting of SEQ ID NO: 1 to SEQ 24.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DETAILED DESCRIPTION OF THE PREFERRED EMBODIMENTS

Figure 1:
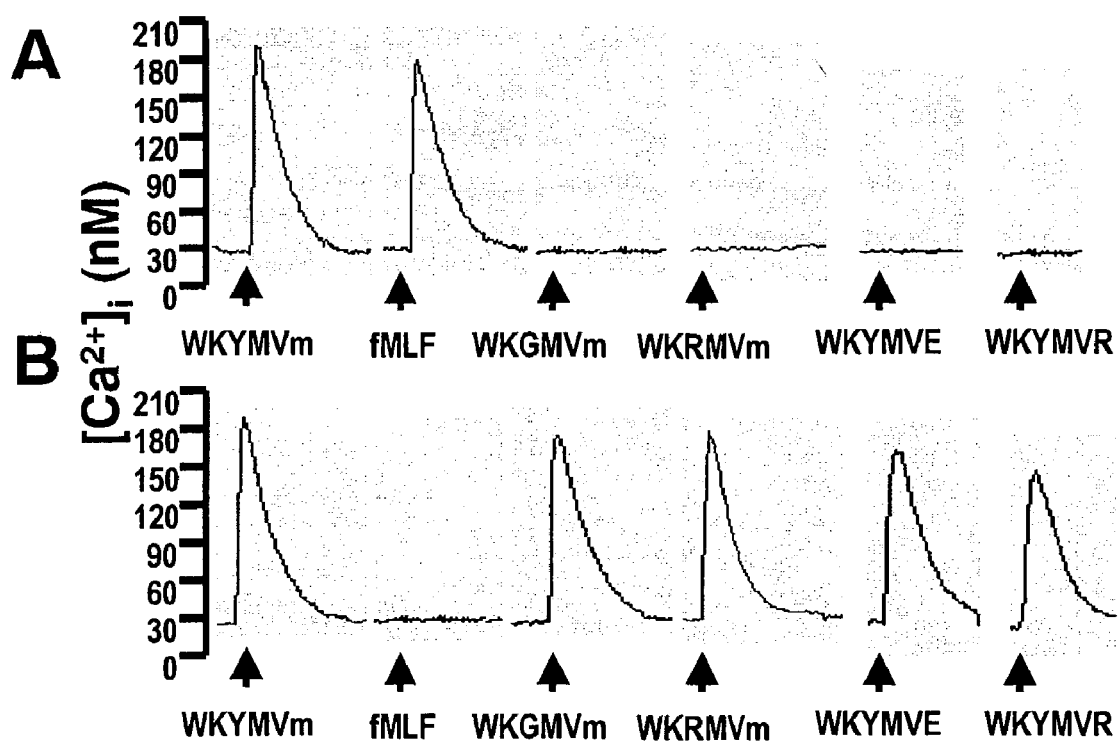
FIG. 1 shows the effect of WKYMVm, the peptides of the present invention (WKGMVm (SEQ ID NO:1), WKRMVm (SEQ ID NO:11), WKYMVE (SEQ ID NO:16), WKYMVR (SEQ ID NO:18)), or fMLF on $[Ca^{2+}]i$ in FPR-expressing RBL-2H3 cells (A) or FPRL1-expressing RBL-2H3 cells (B)

Formyl peptide receptor (FPR) and formyl peptide receptor-like 1 (FPRL1) perform an important role in immune responses. The present invention provides peptides derived from WKYMVm. Many peptides can stimulate FPR or FPRL1 resulting in calcium increase, but the peptides of the present invention such as WKGMVm (SEQ ID NO:1), WKRMVm (SEQ ID NO:11), and $6^{th}$ D-Met substituted peptides effect a calcium increase just in FPRL1-expressing cells but not in FPR-expressing cells. A competition assay using $^{125}$I-WKYMVm shows that not only do many peptides effect a calcium increase in FPR-expressing cells, but WKGMVm (SEQ ID NO:1), WKRMVm (SEQ ID NO:11), and $6^{th}$ D-Met substituted peptides can also compete the binding of $^{125}$I-WKYMVm to FPR. Unlike a phospholipase C-mediated calcium increase, WKGMVm (SEQ ID NO:1), WKRMVm (SEQ ID NO:11), and $6^{th}$ D-Met substituted peptides can stimulate extracellular regulated protein kinase (ERK) and Akt activation in FPR-expressing cells.

Regarding the functional consequences of WKYMVm, the peptide stimulates degranulation and cellular chemotaxis via $Ca^{2+}$ and ERK pathways, respectively, in FPR cells. The peptides such as WKGMVm (SEQ ID NO:1), WKRMVm (SEQ ID NO:11), and $6^{th}$ D-Met substituted peptides, however, stimulated FPR cells by just inducing chemotactic migration but not degranulation. Taken together, it is demonstrated that as an important chemoattractant receptor, FPR can be modulated differentially by distinct peptide ligands in a ligand-specific manner, for the first time.

According to a first preferable embodiment, the peptides of the present invention comprise amino acid sequences selected from the group consisting of SEQ ID NO: 1 to SEQ ID NO: 24 or a substance derived from the peptides of SEQ ID NO: 1 to SEQ ID NO: 24. The SEQ ID NO: 1 to SEQ ID NO: 24 are as follows:

Trp-Lys-Gly-Met-Val-D-Met-NH$_2$ (WKGMVm; SEQ ID NO: 1), Trp-Lys-Tyr-Met-Gly-D-Met-NH$_2$ (WKYMGm; SEQ ID NO: 2) Trp-Lys-Tyr-Met-Val-Gly-NH$_2$ (WKYMVG; SEQ ID NO: 3), Trp-Arg-Tyr-Met-Val-D-Met-NH$_2$ (WRYMVm; SEQ ID NO: 4), Trp-Glu-Tyr-Met-Val-D-Met-NH$_2$ (WEYMVm; SEQ ID NO: 5), Trp-His-Tyr-Met-Val-D-Met-NH$_2$ (WHYMVm; SEQ ID NO: 6), Trp-Asp-Tyr-Met-Val-D-Met-NH$_2$ (WDYMVm; SEQ ID NO: 7), Trp-Lys-His-Met-Val-D-Met-NH$_2$ (WKHMVm; SEQ ID NO: 8), Trp-Lys-Glu-Met-Val-D-Met-NH$_2$ (WKEMVm; SEQ ID NO: 9), Trp-Lys-Trp-Met-Val-D-Met-NH$_2$ (WKWMVm; SEQ ID NO: 10), Trp-Lys-Arg-Met-Val-D-Met-NH$_2$ (WKRMVm; SEQ ID NO: 11), Trp-Lys-Asp-Met-Val-D-Met-NH$_2$ (WKDMVm; SEQ ID NO: 12), Trp-Lys-Phe-Met-Val-D-Met-NH$_2$ (WKFMVm; SEQ ID NO: 13), Trp-Lys-Tyr-Met-Tyr-D-Met-NH$_2$ (WKYMYm; SEQ ID NO: 14), Trp-Lys-Tyr-Met-(Phe/Trp)-D-Met-NH$_2$ (WKYM(F/W)m; SEQ ID NO: 15), Trp-Lys-Tyr-Met-Val-Glu-NH$_2$ (WKYMVE; SEQ ID NO: 16), Trp-Lys-Tyr-Met-Val-Val-NH$_2$ (WKYMVV; SEQ ID NO: 17), Trp-Lys-Tyr-Met-Val-Arg-NH$_2$ (WKYMVR; SEQ ID NO: 18), Trp-Lys-Tyr-Met-Val-Trp-NH$_2$ (WKYMVW; SEQ ID NO: 19), Trp-Lys-Tyr-Met-Val-NH$_2$ (WKYMV; SEQ ID NO: 20), Lys-Tyr-Met-Val-D-Met-NH$_2$ (KYMVm; SEQ ID NO: 21), Lys-Tyr-Met-Val-NH$_2$ (KYMV; SEQ ID NO: 22), Tyr-Met-Val-D-Met-NH$_2$ (YMVm; SEQ ID NO: 23), and Met-Val-D-Met-NH$_2$ (MVm; SEQ ID NO: 24).

The peptides of SEQ ID NO: 1 to SEQ ID NO: 24 exist in isolated and substantially pure form.

The peptides include amino acid residue optionally substituted with an —NH$_2$ group on a carboxyl group.

The peptide of the present invention has at least one of the following properties:
(a) it induces superoxide generation by human monocytes or neutrophils;
(b) it induces an intracellular calcium increase by human peripheral blood monocytes or neutrophils;
(c) it binds to formyl peptide receptor or formyl peptide receptor-like 1;
(d) it induces chemotactic migration of human monocytes or neutrophils in vitro;
(e) it induces degranulation in formyl peptide receptor expressing cells or formyl peptide receptor-like 1 expressing cells;
(f) it stimulates extracellular signal-regulated protein kinase phosphorylation via activation of formyl peptide receptor or formyl peptide receptor-like 1; and
(g) it stimulates Akt phosphorylation via activation of formyl peptide receptor or formyl peptide receptor-like 1.

According to a second preferable embodiment, the present invention provides a pharmaceutical composition comprising a peptide of which the amino acid sequence is selected from the group consisting of SEQ ID NO: 1 to SEQ ID NO: 24; or a substance derived from the peptide of which the amino acid sequence is selected from the group consisting of SEQ ID NO: 1 to SEQ ID NO: 24.

The composition comprising the peptide or the substance as an active ingredient can include more than one kind of pharmaceutical diluent, selected from the group consisting of saline, buffered saline, dextrose, water, glycerol, and ethanol, but the diluent is not limited thereto.

The composition may be applied differently according to the purpose of dosing and the disease. It should be understood that the amount of the active ingredient actually administered ought to be determined in light of various relevant factors, including the condition to be treated, the severity of the patient's symptoms, co-administration with other drugs (e.g., chemotherapeutic agents), age, sex, body weight of the individual patient, food, dosing time, the chosen route of administration, and the ratio of the composition. The composition may be administered in a single or in 1–3 divided doses per day, even though the dose and route of administration are adjusted to the type and severity of disease.

The composition comprising the peptide or the substance of the present invention can be administered via oral or parenteral routes. Parenteral dosing means the administration of a drug through a route other than oral, which includes rectal, intravenous, intraperitoneal and intramuscular, intra-arterial, transdermal, nasal, inhalation, ocular, and subcutaneous introduction.

Pharmaceutical formulations containing the peptide or the substance may be prepared in any form, such as oral dosage form, injectable solution, or topical preparation. The formulation can be preferably prepared for oral and injectable administration (true solution, suspension, or emulsion) and most preferably in oral form such as tablet, capsule, soft capsule, aqueous medicine, pill, granule, and the like.

In preparing the formulation, the peptides are filled in a soft capsule without any excipient, or formed as an appropriate formulation after mixing or diluting with a carrier. Examples of suitable carriers are starches, water, saline, Ringer's solution, dextrose, etc.

According to a third preferable embodiment of the present invention, a method of treating conditions accompanied or caused by modification of the number or activation states of leukocytes is provided. The method comprises administering to a host in need of such treatment a therapeutically effective amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24. The condition may be bacterial, mycoplasma, yeast, fungal, a viral infection, or inflammation.

According to a fourth preferable embodiment of the present invention, a method of increasing the number or raising the activation state of leukocytes is provided. The method comprises administering to a host in need of a greater number or higher activation state of leukocytes a therapeutically effective amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24.

According to a fifth preferable embodiment of the present invention, a method of inducing extracellular calcium increase in leukocytes in a patient in need of such treatment is provided. The method comprises administering to said patient an amount of a peptide having an amino acid sequence selected from the group consisting of SEQ ID NO: 1 to SEQ ID NO: 24 in an amount effective to therapeutically or prophylactically achieve such induction or desensitization.

According to a sixth preferable embodiment of the present invention, a method of inducing superoxide generation by human monocytes or neutrophils in a patient in need of such treatment is provided. The method comprises administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

According to a seventh preferable embodiment of the present invention, a method of inducing chemotactic migration by human peripheral blood mononuclear cells in a patient in need of such treatment is provided. The method comprises administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

According to an eighth preferable embodiment of the present invention, a method of inducing degranulation in formyl peptide receptor or formyl peptide receptor-like 1 expressing cells in a patient in need of such treatment is provided. The method comprises administering to said patient an amount of a peptide having an amino acid sequences selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

According to a ninth preferable embodiment of the present invention, a method of competing peptides with WKYMVm for binding formyl peptide receptor or a formyl peptide receptor-like 1 in the formyl peptide receptor expressing cells or the formyl peptide receptor-like 1 expressing cells, respectively, in a patient in need of such treatment is provided. The method comprises administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

According to a tenth preferable embodiment of the present invention, a method of stimulating extracellular signal regulated protein kinase in formyl peptide receptor or formyl peptide receptor-like 1 expressing cells in a patient in need of such treatment is provided. The method comprises administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

According to an eleventh preferable embodiment of the present invention, a method of stimulating Akt in formyl peptide receptor or formyl peptide receptor-like 1 expressing cells in a patient in need of such treatment is provided. The method comprises administering to said patient an amount of a peptide having an amino acid sequence selected from the group consisting of SEQ ID NO: 1 to SEQ ID NO: 24 or a substance derived from the peptide of which the amino acid sequence is selected from the group consisting of SEQ ID NO: 1 to SEQ ID NO: 24 in an amount effective to therapeutically or prophylactically achieve such induction or desensitization.

In the above third to eleventh preferable embodiments, the treated host or patient may be one afflicted with a disorder caused by infection, particularly cytomegalovirus infection, rheumatoid arthritis, Lyme's arthritis, gout, sepsis syndrome, hyperthermia, ulcerative colitis, enterocolitis, osteoporosis, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

The present invention provides an isolated nucleotide encoding a peptide having an amino acid sequence comprising SEQ ID NO: 1 to SEQ ID NO: 24.

The present invention provides a vector comprising an isolated nucleotide encoding a peptide having an amino acid sequence comprising SEQ ID NO: 1 to SEQ ID NO: 24.

The present invention provides a polypeptide comprising an amino acid sequence selected from SEQ ID NO: 1 to SEQ ID NO: 24.

The present invention is further explained in more detail with reference to the following examples. These examples, however, should not in any sense be interpreted as limiting the scope of the present invention.

Materials Used in the Examples

Fmoc amino acids were obtained from Millipore (Bedford, Mass.). Rapidamide resin was purchased from Dupont (Boston, Mass.). Peripheral blood mononuclear cell (PBMC) separation medium (Histopaque-1077), cytochrome c, and fMLF were purchased from Sigma (St. Louis, Mo.). Fura-2 pentaacetoxymethylester (fura-2/AM) was purchased from Molecular Probes (Eugene, Oreg.). RPMI 1640 was obtained from Life Technologies (Grand Island, N.Y.). Dialyzed fetal bovine serum and supplemented bovine serum were purchased from Hyclone Laboratories Inc. (Logen, Utah). PTX, GF109203X, and PD98059 were purchased from Calbiochem (San Diego, Calif.). LY294002 was purchased from BIOMOL research laboratories, Inc. (Polymouth Meeting, Pa.).

The peptides were synthesized by the solid-phase method described above. Back, S. H., Seo, J. K., Chae, C. B., Suh, P. G., and Ryu, S. H. (1996) J. Biol. Chem. 271, 8170–8175; Seo, J. K., Choi, S. Y., Kim, Y., Baek, S. H., Kim, K. T., Chae, C. B., Lambeth, J. D., Suh, P. G., and Ryu, S. H. (1997) J. Immunol. 158, 1895–1901. Briefly, peptides were synthesized on a rapidamide support resin and assembled following the standard Fmoc/t-butyl strategy on an acid-labile linker. The composition of the peptides was confirmed by amino acid analysis as described previously. Back, S. H., Seo, J. K., Chae, C. B., Suh, P. G., and Ryu, S. H. (1996) J. Biol. Chem. 271, 8170–8175.

RBL-2H3, FPR-expressing RBL-2H3, and FPRL1-expressing RBL-2H3 cells were cultured with DMEM supplemented with 20% FBS and 200 g/ml of G418 as described above. He, R., Tan, L., Browning, D. D., Wang, J. M., and Ye, R. D. (2000) J. Immunol. 165, 4598–4605.

EXAMPLE 1

Isolation of Neutrophils

Peripheral blood leukocyte concentrates were donated by the Ulsan Red Cross Blood Center (Ulsan, Korea). Human neutrophils were isolated according to the standard procedures of dextran sedimentation, hypotonic lysis of erythrocytes, and a lymphocyte separation medium gradient as described above. Seo, J. K., Choi, S. Y., Kim, Y., Baek, S. H., Kim, K. T., Chae, C. B., Lambeth, J. D., Suh, P. G., and Ryu, S. H. (1997) J. Immunol. 158, 1895–1901. The isolated human neutrophils were then used promptly.

EXAMPLE 2

Effect of Peptides on Superoxide Generation in Human Neutrophils

The activity of the peptides, WKYMVm, peptides of SEQ ID NOs: 1 to 24, and wkymvm on superoxide generation in human neutrophils was measured. Superoxide anion generation was quantified by measuring reduction of cytochrome c using a microtiter 96-well plate ELISA reader (Bio-Tekinstruments, EL312e, Winooski, Vt.) as described. Bae, Y. S., Bae, H., Kim, Y., Lee, T. G., Suh, P. G., and Ryu, S. H. (2001) Blood 97, 2854–2862. The human neutrophils ($1 \times 10^6$ cells/100 μl of RPMI 1640 medium per well of a 96-well plate) were preincubated with 50 μM cytochrome c at 37° C. for 1 min and then incubated with the indicated concentrations of peptides. The superoxide generation was measured as a change in light absorption at 550 nm over 5 minutes at 1 min intervals. From at least four independent experiments, peptides with active amino acids at each position were chosen. These results are shown in Table I.

Stimulation of neutrophils with various concentrations of the peptide, WKYMVm caused superoxide generation in a concentration-dependent manner, showing the maximal activity with 100 nM of the peptide (data not shown). While some of the peptides such as WRYMVm (SEQ ID NO:4), WEYMVm (SEQ ID NO:5), WKFMVm (SEQ ID NO:13), and KYMVm (SEQ ID NO:21) stimulated superoxide generation in the cells, many of the peptides were weaker regarding activity on superoxide generating activity with 100 nM of peptides.

TABLE I

Effect of Peptides On Superoxide Generation In Human Nutrophils[a]

| SEQ ID NO | Sequence[b] | $O^{2-}$ (nmol/$10^6$ cells) | SEQ ID NO | Sequence | $O^{2-}$ (nmol/$10^6$ cells) |
|---|---|---|---|---|---|
|    | WKYMVm-$NH_2$ | 37.3 ± 6.94 | 13 | WKFMVm-$NH_2$ | 37.3 ± 3.56 |
| 1  | WKGMVm-$NH_2$ | 14.2 ± 3.42 | 14 | WKYMYm-$NH_2$ | 25.8 ± 3.89 |
| 2  | WKYMGm-$NH_2$ | 1.1 ± 0.05 | 15 | WKYM(F/W)m-$NH_2$ | 6.1 ± 0.77 |
| 3  | WKYMVG-$NH_2$ | 4.4 ± 0.54 | 16 | WKYMVE-$NH_2$ | 5.0 ± 0.43 |
| 4  | WRYMVm-$NH_2$ | 47.1 ± 11.23 | 17 | WKYMVV-$NH_2$ | 5.0 ± 0.21 |
| 5  | WEYMVm-$NH_2$ | 52.9 ± 12.78 | 18 | WKYMVR-$NH_2$ | 16.3 ± 1.57 |
| 6  | WHYMVm-$NH_2$ | 20.7 ± 7.85 | 19 | WKYMVW-$NH_2$ | 11.5 ± 1.62 |
| 7  | WDYMVm-$NH_2$ | 25.8 ± 6.56 | 20 | WKYMV-$NH_2$ | 9.2 ± 0.55 |
| 8  | WKHMVm-$NH_2$ | 29.5 ± 7.71 | 21 | KYMVm-$NH_2$ | 36.0 ± 3.56 |
| 9  | WKEMVm-$NH_2$ | 4.1 ± 0.21 | 22 | KYMV-$NH_2$ | 7.5 ± 0.61 |
| 10 | WKWMVm-$NH_2$ | 11.5 ± 0.97 | 23 | YMVm-$NH_2$ | 30.2 ± 2.74 |
| 11 | WKRMVm-$NH_2$ | 15.9 ± 2.48 | 24 | MVm-$NH_2$ | 0 |
| 12 | WKDMVm-$NH_2$ | 16.3 ± 1.67 |    | wkymvm-$NH_2$ | 0 |

[a]Superoxide generation was measured by monitoring cytochrome c reduction.
[b]The concentration of the treated peptide was 100 nM.

The effect of the peptides on superoxide generation with a 10 μM concentration was also measured. The results are shown in Table II. All of the peptides except wkymvm stimulated superoxide generation as potent as WKYMVm with a 10 μM concentration. Among the peptides, WKWMVm (SEQ ID NO:10), WKFMVm (SEQ ID NO:13), and WKYMVW (SEQ ID NO:19) showed more potent activity than WKYMVm.

TABLE II

Effect of peptides on superoxide generation in human neutrophils[a]

| SEQ ID NO | Sequence[b] | $O^{2-}$ (nmol/$10^6$ cells) | SEQ ID NO | Sequence | $O^{2-}$ (nmol/$10^6$ cells) |
|---|---|---|---|---|---|
|    | WKYMVm-$NH_2$ | 39.0 ± 3.58 | 13 | WKFMVm-$NH_2$ | 60.2 ± 5.57 |
| 1  | WKGMVm-$NH_2$ | 37.6 ± 4.57 | 14 | WKYMYm-$NH_2$ | 42.9 ± 3.34 |
| 2  | WKYMGm-$NH_2$ | 27.3 ± 2.61 | 15 | WKYM(F/W)m-$NH_2$ | 45.6 ± 7.76 |
| 3  | WKYMVG-$NH_2$ | 27.3 ± 1.40 | 16 | WKYMVE-$NH_2$ | 33.6 ± 6.43 |
| 4  | WRYMVm-$NH_2$ | 38.2 ± 6.54 | 17 | WKYMVV-$NH_2$ | 36.3 ± 2.29 |
| 5  | WEYMVm-$NH_2$ | 35.3 ± 2.88 | 18 | WKYMVR-$NH_2$ | 44.8 ± 3.65 |
| 6  | WHYMVm-$NH_2$ | 20.7 ± 7.85 | 19 | WKYMVW-$NH_2$ | 56.8 ± 4.60 |
| 7  | WDYMVm-$NH_2$ | 37.3 ± 5.66 | 20 | WKYMV-$NH_2$ | 25.6 ± 2.20 |
| 8  | WKHMVm-$NH_2$ | 39.3 ± 4.10 | 21 | KYMVm-$NH_2$ | 49.2 ± 5.82 |
| 9  | WKEMVm-$NH_2$ | 39.2 ± 4.71 | 22 | KYMV-$NH_2$ | 35.4 ± 2.13 |
| 10 | WKWMVm-$NH_2$ | 65.0 ± 12.10 | 23 | YMVm-$NH_2$ | 41.8 ± 3.46 |
| 11 | WKRMVm-$NH_2$ | 41.7 ± 8.32 | 24 | MVm-$NH_2$ | 42.4 ± 2.47 |
| 12 | WKDMVm-$NH_2$ | 37.3 ± 2.78 |    | wkymvm-$NH_2$ | 0 |

[a]Superoxide generation was measured by monitoring cytochrome c reduction.
[b]The concentration of the treated peptide was 10 μM.

EXAMPLE 3

Effect of the Peptides on [$CA^{2+}$]i Increase in FPR- or in FPRL1-Expressing RBL-2H3 Cells The activity of the peptides, WKYMVm, peptides of SEQ ID NOs: 1 to 24, and wkymvm on [$Ca^{2+}$]i increase was measured in FPR-expressing RBL-2H3 cells. FPR-expressing RBL-2H3 cells were stimulated with 10 μM of each peptide, and [$Ca^{2+}$]i was determined. The level of [$Ca^{2+}$]i was determined fluorometrically by Grynkiewicz's method using fura-2/AM. Grynkiewicz, G., Poenie, M., and Tsien, R. Y. (1986) J. Biol. Chem. 260, 3440–3450. Briefly, prepared cells were incubated with 3 μM fura-2/AM at 37° C. for 50 min in a fresh serum-free RPMI 1640 medium under continuous stirring. 2×$10^6$ cells were aliquoted for each assay in $Ca^{2+}$-free Locke's solution (154 mM NaCl, 5.6 mM KCl, 1.2 mM $MgCl_2$, 5 mM HEPES, pH 7.3, 10 mM glucose, and 0.2 mM EGTA). Fluorescence changes at the dual excitation wavelengths of 340 nm and 380 nm and the emission wavelength of 500 nm were measured, and the calibrated fluorescence ratio was translated into [$Ca^{2+}$]i. The peak level of the increased [$Ca^{2+}$]i was monitored. The results are shown in Table III and FIG. 1A. Data are representative of three independent experiments.

TABLE III

Effect of peptides on intracellular calcium increase in FPR-expressing RBL-2H3 cells[a]

| SEQ ID NO | Sequence | EC50 (nM) | SEQ ID NO | Sequence | EC50 (nM) |
|---|---|---|---|---|---|
|  | WKYMVm-NH$_2$ | 47.4 ± 10.94 | 13 | WKFMVm-NH$_2$ | 17.7 ± 4.79 |
| 1 | WKGMVm-NH$_2$ | inactive | 14 | WKYMYm-NH$_2$ | 665.4 ± 81.53 |
| 2 | WKYMGm-NH$_2$ | inactive | 15 | WKYM(F/W)m-NH$_2$ | 57.3 ± 10.30 |
| 3 | WKYMVG-NH$_2$ | inactive | 16 | WKYMVE-NH$_2$ | inactive |
| 4 | WRYMVm-NH$_2$ | 54.9 ± 8.33 | 17 | WKYMVV-NH$_2$ | inactive |
| 5 | WEYMVm-NH$_2$ | 317.4 ± 29.33 | 18 | WKYMVR-NH$_2$ | inactive |
| 6 | WHYMVm-NH$_2$ | 31.7 ± 3.36 | 19 | WKYMVW-NH$_2$ | inactive |
| 7 | WDYMVm-NH$_2$ | 98.9 ± 17.51 | 20 | WKYMV-NH$_2$ | inactive |
| 8 | WKHMVm-NH$_2$ | 279.8 ± 35.86 | 21 | KYMVm-NH$_2$ | 384.8 ± 33.13 |
| 9 | WKEMVm-NH$_2$ | 1332.8 ± 88.75 | 22 | KYMV-NH$_2$ | inactive |
| 10 | WKWMVm-NH$_2$ | 18.8 ± 5.31 | 23 | YMVm-NH2 | 569.1 ± 63.38 |
| 11 | WKRMVm-NH$_2$ | inactive | 24 | MVm-NH2 | inactive |
| 12 | WKDMVm-NH$_2$ | 1329.5 ± 207.20 |  | wkymvm-NH2 | inactive |

In FPR-expressing RBL-2H3 cells, the peptide WKYMVm induced a [Ca$^{2+}$]i increase in a concentration-dependent manner, showing maximal activity around 300 nM (data not shown). EC$_{50}$ of the WKYMVm for [Ca$^{2+}$]i-increasing activity in FPR cells was 47 nM (Table III). Among the peptides of the present invention, while WHYMVm, WKWMVm (SEQ ID NO:10), and WKFMVm (SEQ ID NO:13) showed more improved affinity for the FPR against the peptide WKYMVm, the other peptides were not as active as WKYMVm (Table III). In particular, WKGMVm (SEQ ID NO:1), WKYMGm (SEQ ID NO:2), and 6th D-Met substituted peptides did not effect a [Ca$^{2+}$]i increase until 20 μM treatment in FPR-expressing RBL-2H3 cells (Table III and FIG. 1A). N-terminal- or C-terminal-truncated peptides are also inactive for the [Ca$^{2+}$]i increasing activity in FPR cells (Table III). These results suggest that Tyr$^3$ and D-Met$^6$ are critical for the activation of FPR in [Ca$^{2+}$]i increase.

The effect of the peptides, WKYMVm, peptides of SEQ ID NOs: 1 to 24, and wkymvm on [Ca$^{2+}$]i increase was checked in FPRL1-expressing RBL-2H3 cells. FPRL1-expressing RBL-2H3 cells were stimulated with 10 μM of each peptide, and [Ca$^{2+}$]i was determined. The level of [Ca$^{2+}$]i was determined by the same procedures as above. The peak level of the increased [Ca$^{2+}$]i was monitored. The results are shown in Table IV and FIG. 1B. Data are representative of three independent experiments.

In FPRL1-expressing RBL-2H3 cells, WKYMVm showed maximal activity with a 10 nM concentration (data not shown). EC$_{50}$ of the WKYMVm for [Ca$^{2+}$]i-increasing activity in FPRL1 cells was 0.6 nM (Table IV). Unlike in FPR cells, all the peptides were active on [Ca$^{2+}$]i-increasing activity in FPRL1 cells (Table IV). Some of the peptides, such as WRYMVm (SEQ ID NO:4), WKWMVm (SEQ ID NO:10), WKFMVm (SEQ ID NO:13), WKYMYm (SEQ ID NO:14), and WKYM(F/W)m (SEQ ID NO:15), showed a higher affinity to FPRL1 (Table IV). WKGMVm (SEQ ID NO:1), WKYMGm (SEQ ID NO:2), and 6th D-Met-substituted peptides that could not effect a [Ca$^{2+}$]i increase in FPR cells also showed [Ca$^{2+}$]i-increasing activity in FPRL1 cells, with a little lower affinity to FPRL1 (Table IV and FIG. 1B). N-terminal or C-terminal truncated pepeides also stimulated a [Ca$^{2+}$]i increase in FPRL1 cells (Table IV). These results indicate that Tyr$^3$ and D-Met$^6$ are less critical for the activation of FPRL1 against FPR resulting in a [Ca$^{2+}$]i increase.

TABLE IV

Effect of peptides on intracellular calcium increase in FPRL1-expressing RBL-2H3 cells[a]

| SEQ ID NO | Sequence | EC50 (nM) | SEQ ID NO | Sequence | EC50 (nM) |
|---|---|---|---|---|---|
|  | WKYMVm-NH$_2$ | 0.60 ± 0.090 | 13 | WKFMVm-NH$_2$ | 0.23 ± 0.042 |
| 1 | WKGMVm-NH$_2$ | 21.32 ± 2.104 | 14 | WKYMYm-NH$_2$ | 0.29 ± 0.061 |
| 2 | WKYMGm-NH$_2$ | 18.11 ± 1.308 | 15 | WKYM(F/W)m-NH$_2$ | 0.12 ± 0.015 |
| 3 | WKYMVG-NH$_2$ | 5945.8 ± 176.100 | 16 | WKYMVE-NH$_2$ | 502.87 ± 64.965 |
| 4 | WRYMVm-NH$_2$ | 0.12 ± 0.010 | 17 | WKYMVV-NH$_2$ | 1259.15 ± 95.750 |
| 5 | WEYMVm-NH$_2$ | 5.23 ± 0.196 | 18 | WKYMVR-NH$_2$ | 177.52 ± 26.035 |
| 6 | WHYMVm-NH$_2$ | 0.72 ± 0.075 | 19 | WKYMVW-NH$_2$ | 194.48 ± 19.210 |
| 7 | WDYMVm-NH$_2$ | 14.28 ± 1.225 | 20 | WKYMV-NH$_2$ | 917.85 ± 45.610 |
| 8 | WKHMVm-NH$_2$ | 1.94 ± 0.268 | 21 | KYMVm-NH$_2$ | 3.01 ± 0.232 |
| 9 | WKEMVm-NH$_2$ | 28.30 ± 1.354 | 22 | KYMV-NH$_2$ | >30000 |
| 10 | WKWMVm-NH$_2$ | 0.16 ± 0.027 | 23 | YMVm-NH$_2$ | 17.15 ± 0.889 |
| 11 | WKRMVm-NH$_2$ | 2.06 ± 0.256 | 24 | MVm-NH$_2$ | >30000 |
| 12 | WKDMVm-NH$_2$ | 8.73 ± 1.210 |  | wkymvm-NH$_2$ | inactive |

[a]Intracellular calcium increase was monitored from fura-2 loaded cells.

EXAMPLE 4

Effect of the Peptides on [$^{125}$I] WKYMVM Binding to FPR or FPRL1

From the finding that some of the peptides (WKGMVm (SEQ ID NO:1), WKRMVm (SEQ ID NO:11), D-Met$^6$ substituted peptides) could not induce a cytosolic calcium increase, it was checked whether the peptides can bind to FPR or not. Displacement of $^{125}$I-labeled WKYMVm binding to FPR or FPRL1 by the peptides was monitored. FPR-expressing RBL-2H3 cells were incubated with [$^{125}$I] WKYMVm in the absence or presence of increasing amounts of unlabeled WKYMVm or the peptides of SEQ ID NOs: 1 to 24.

A ligand binding analysis was performed as modified from the previous report. Hu, J. Y., Le, Y., Gong, W., Dunlop, N. M., Gao, J. L., Murphy, P. M., and Wang, J. M. (2001) J. Leukoc. Biol. 70, 155–1561. The radioiodinated WKYMVm ($^{125}$I-labeled) was purchased from NEN Lifesciences (Boston, Mass.). Briefly, FPR- or FPRL1-expressing RBL-2H3 cells were seeded into 1×10$^5$ cells per well of a 24-well plate and cultured overnight. After blocking the cells with a blocking buffer (33 mM HEPES, pH 7.5, 0.1% BSA in RPMI) for 2 hr, a single concentration of $^{125}$I-labeld WKYMVm was added to cells with a binding buffer (PBS containing 0.1% BSA) in the absence or presence of 50 μM unlabelled peptides and incubated for 3 hr at 4° C. with continuous shaking. Then the samples were washed 5 times with ice-cold binding buffer, and 200 μl of lysis buffer (20 mM Tris, pH 7.5, 1% Triton X-100) was added to each well. After 20 min of lysis at room temperature, the lysates were collected. Bound $^{125}$I-labeled WKYMVm was measured for radioactivity for a γ-ray counter.

Figure 2:
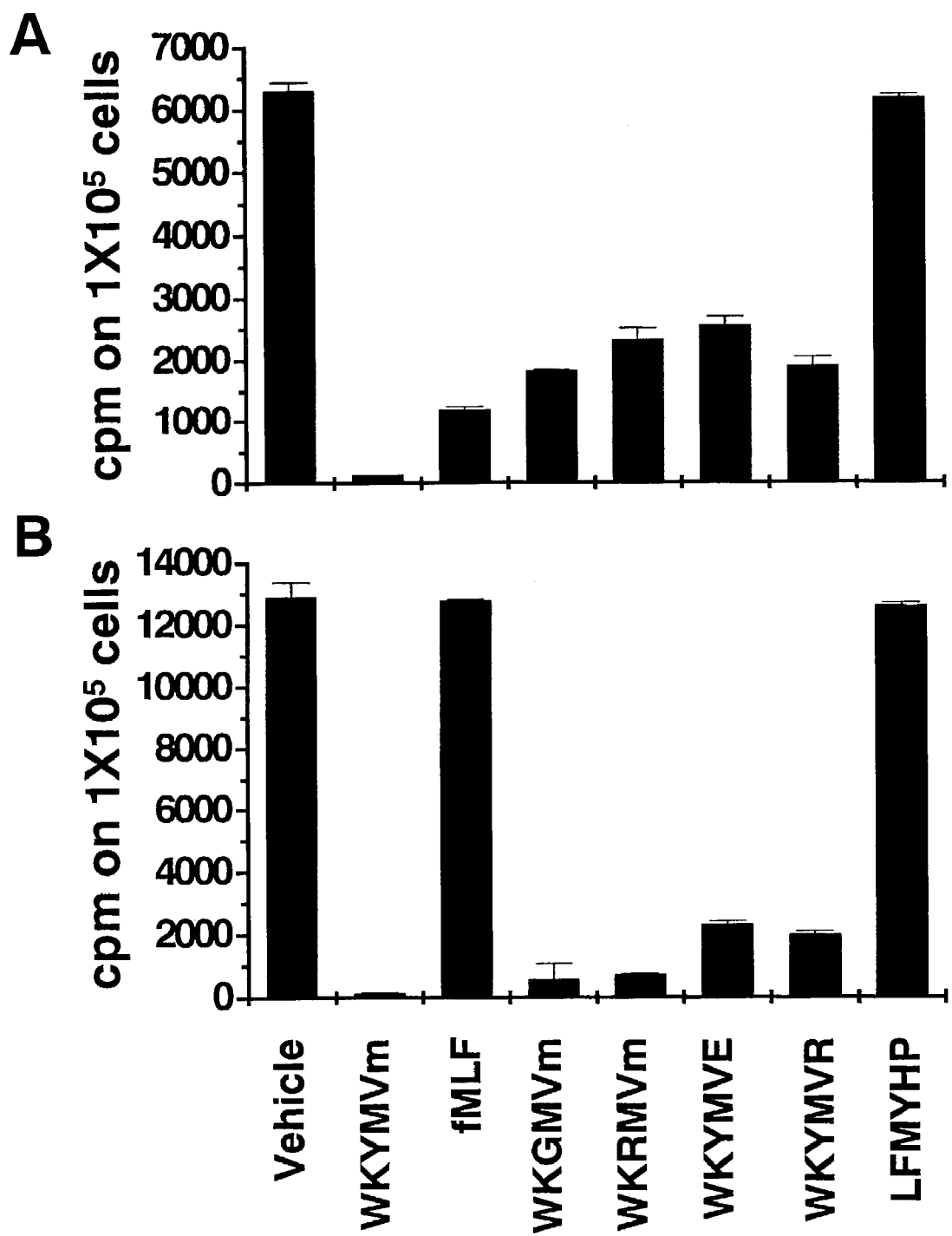
FIG. 2 shows Displacement of $^{125}$I-labeled WKYMVm binding to FPR or FPRL1 by WKYMVm, the peptides of the present invention (WKGMVm (SEQ ID NO:1), WKRMVm (SEQ ID NO:11), WKYMVE (SEQ ID NO:16), WKYMVR (SEQ ID NO:18)), and fMLF.

Ligand binding analysis results are shown in FIG. 2. As shown in FIG. 2, not only unlabeled WKYMVm but also WKGMVm (SEQ ID NO:1), WKRMVm (SEQ ID NO:11), and D-Met6 substituted peptides of WKYMVm inhibited binding of [$^{125}$I] WKYMVm in a concentration-dependent manner. These results indicate that although WKGMVm (SEQ ID NO:1), WKRMVm (SEQ ID NO:11), or D-Met$^6$-substituted peptides of WKYMVm could bind to FPR, all the peptides could not induce cytosolic calcium increase in FPR-expressing RBL cells.

EXAMPLE 5

Effect of the Peptides on ERK Phosphorylation in FPR or RPRL1 Expressing RBL-2H3 Cells i) Stimulation of Cells with Peptides Cultured RBL-2H3 cells were aliquoted into 2×10$^6$ cells and stimulated with the indicated concentrations of WKYMVm and the peptides of the present invention for the indicated lengths of time. FPR- or FPRL1-expressing RBL-2H3 cells were stimulated with 1 μM WKYMVm for various periods of time (FIG. 3A). Two cells were preincubated with a vehicle or 100 ng/ml of PTX (24 hr), 50 μM of LY294002 (15 min), 5 μM of GFX (15 min), 10 μM BAPTA/AM (60 min), or 50 μM PD98059 (60 min) prior to 1 μM of WKYMVm treatment (FIG. 3B). FPR- or FPRL1-expressing RBL2H3 cells were stimulated with 10 μM of the peptides of the present invention for 2 min or 5 min, respectively (FIG. 3C).

After stimulation, the cells were washed with serum-free RPMI and lysed in a lysis buffer (20 mM Hepes, pH 7.2, 10% glycerol, 150 mM NaCl, 1% Triton X-100, 50 mM NaF, 1 mM Na3VO4, 10 μg/ml leupeptin, 10 μg/ml aprotinin, and 1 mM phenylmethylsulfonyl fluoride). The detergent-insoluble materials were pelleted by centrifugation (12,000×g, 15 min, at 4° C.), and the soluble supernatant fraction was removed and stored at −80° C. or used immediately. Protein concentrations in the lysates were determined using the Bradford protein assay reagent.

ii) Electrophoresis and Immunoblot Analysis

Each sample (30 g of protein) was subjected to 10% SDS-PAGE and phosphorylated ERK was determined by an immunoblot analysis with an anti-phospho-ERK antibody. Protein samples were prepared for electrophoresis by addition of a concentrated sample buffer. The portions in the samples were then separated by an 10% SDS-polyacrylamide gel using the buffer system described by Laemmli. King, J., and Laemmli, U. K. (1971) J. Mol. Biol. 62, 465–477.

Following the electrophoresis, a western blot analysis with an anti-ERK2 antibody was performed to confirm that the same amounts of samples were used for the experiments. The proteins were blotted onto nitrocellulose membranes. The nitrocellulose membranes were then blocked by incubation with TBS (Tris-buffered saline, 0.05% Tween-20) containing 5% non-fat dry milk. Subsequently, the membranes were incubated with anti-phospho-ERK antibody, anti-phospho-Akt antibody or anti-Akt antibody washed with TBS. For a PKC translocation assay, an antibody for PKC isozyme-specific was incubated. Antigen-antibody complexes were visualized after incubating the membrane with a 1:5000 diluted goat anti-rabbit IgG or goat anti-mouse IgG antibody coupled to horseradish peroxidase and using the enhanced chemiluminescence detection system.

iii) Results

Figure 3:
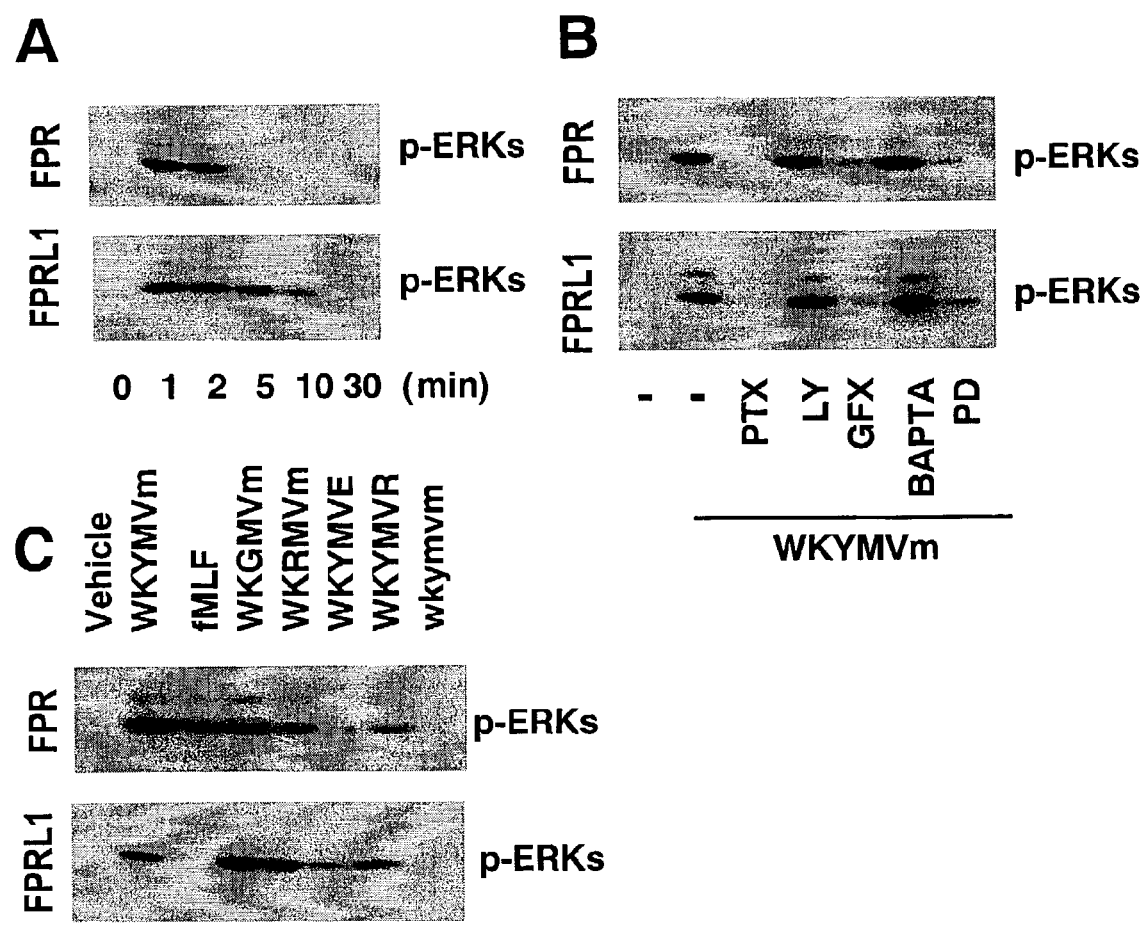
FIG. 3 shows the effect of WKYMVm, the peptides of the present invention (WKGMVm (SEQ ID NO:1), WKRMVm (SEQ ID NO:11), WKYMVE (SEQ ID NO:16), WKYMVR (SEQ ID NO:18)), fMLF, and wkymvm on ERK phosphorylation in FPR- or FPRL1-expressing RBL-2H3 cells.

The effect of the peptides on cellular signaling via FPR or RPRL1 in FPR- or FPRL1-expressing RBL-2H3 cells was evaluated, and the results are shown FIG. 3. Results of FIG. 3 are representative of 3 independent experiments.

Since, although some peptides could bind to FPR, they could not stimulate a PLC-mediated calcium increase, their effect on other signaling (ERKs and Akt) that are independent on PLC in the downstream of some GPCRs was checked. Stimulation of FPR- or FPRL1-expressing RBL-2H3 cells with 1 μM WKYMVm induced transient activation of ERKs showing the maximal activity in 2 min or 5 min after peptide treatment, respectively (FIG. 3A). When FPR- or FPRL1-expressing RBL-2H3 cells were pretreated with several inhibitors prior to WKYMVm stimulation, WKYMVm-induced ERKs activation was sensitive to PTX, and PD98059 indicating that this event is PTX-sensitive G-protein(s) and MEK-dependent (FIG. 3B). Pretreatment of a PI3K inhibitor (LY294002), PKC inhibitors (GF109203X or Ro-31-8220), or a calcium chelator (BAPTA/AM) could not effect WKYMVm-induced ERK activation (FIG. 3B). This suggests that this event is independent on PI3K, Ca$^{2+}$, and PKC activation. So it appears as if WKYMVm induces a [$Ca^{2+}$]i increase and ERK activation via independent signaling pathways. The effect of the peptides of the present invention on ERK activation was checked by Western blot analysis with anti-phospho-ERKs antibody. Unlike cytosolic calcium increasing activity, the peptides (WKGMVm (SEQ ID NO:1), WKRMVm (SEQ ID NO:11), WKYMVR (SEQ ID NO:18), and WKYMVE (SEQ ID NO:16)) stimulated ERKs phosphorylation in FPR-expressing RBL-2H3 cells (FIG. 3C). Keeping in mind that the peptides could not affect on PLC-mediated [$Ca^{2+}$]i increasing activity, this is a very interesting result. When FPRL1-expressing RBL-2H3 cells were stimulated with WKYMVm and the peptides of the present invention, most of the peptides also caused ERKs phosphorylation in FPRL1 cells (FIG. 3C). This result correlates with the previous result that all of the peptides can stimulate a cytosolic calcium increase in FPRL1-expressing cells (FIG. 1B).

EXAMPLE 6

Effect of the Peptides on AKT Phosphorylation in FPR- or RPRL1-Expressing RBL-2H3 Cells It is well known that activation of chemoattractant receptors induces Akt activation via PI3K. Franke, T. F., Yang, S. I., Chan, T. O., Datta, K., Kazlauskas, A., Morrison, D. K., Kaplan, D. R., and Tsichlis, P. N. (1995) Cell. 81, 727–736. Stimulation of cells with the peptides, electrophoresis and immunoblot analysis were performed according to the same method as in Example 5.

Figure 4:
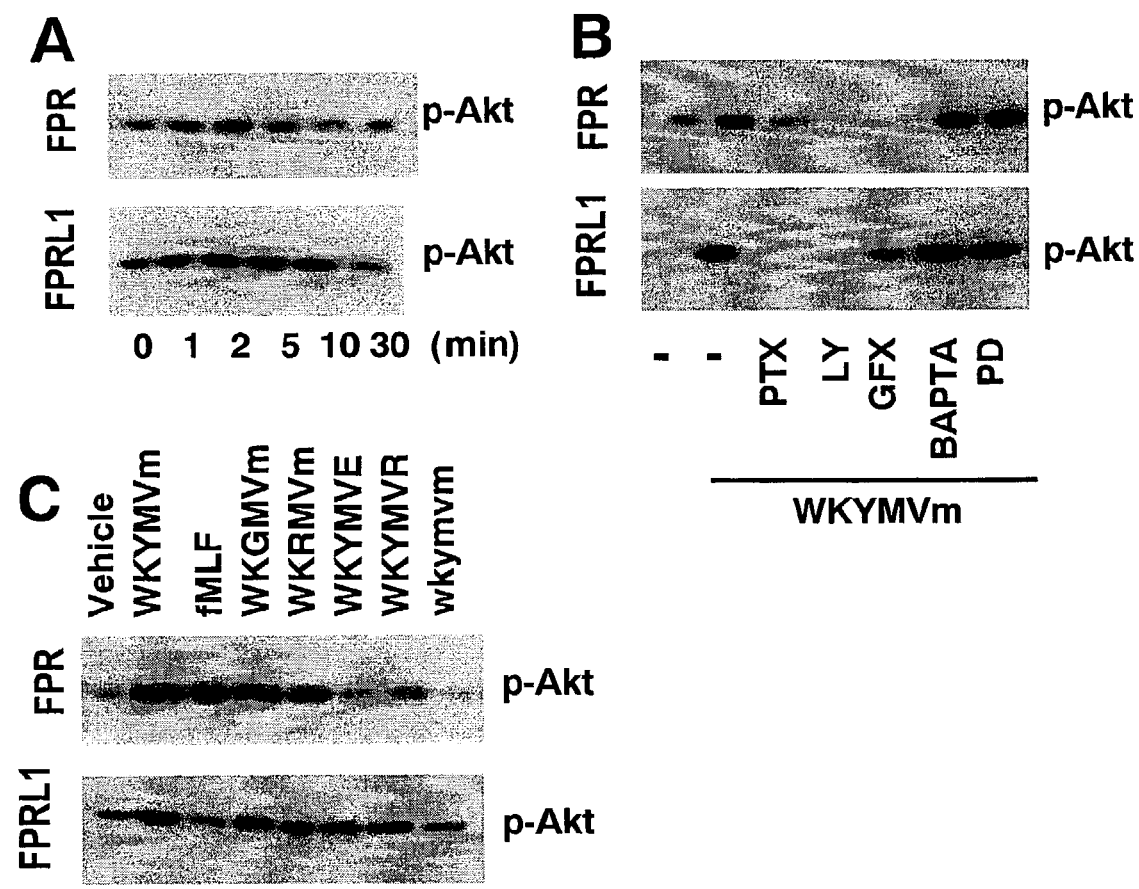
FIG. 4 shows the effect of WKYMVm, the peptides of the present invention (WKGMVm (SEQ ID NO:1), WKRMVm (SEQ ID NO:11), WKYMVE (SEQ ID NO:16), WKYMVR (SEQ ID NO:18)), fMLF, and wkymvm on Akt phosphorylation in FPR- or FPRL1-expressing RBL-2H3 cells.

FPR- or FPRL1-expressing RBL-2H3 cells were stimulated with 1 μM WKYMVm for various periods of time (FIG. 4A). Two cells were preincubated with a vehicle or 100 ng/ml of PTX (24 hr), 50 μM of LY294002 (15 min), 5 μM of GFX (15 min), 10 μM BAPTA/AM (60 min), or 50 μM PD98059 (60 min) prior to treatment with 1 μM of WKYMVm (FIG. 4B). FPR- and FPRL1-expressing RBL2H3 cells were stimulated with 10 μM of WKYMVm and the present peptides for 2 min or 5 min, respectively (FIG. 4C). Each sample (30 μg of protein) was subjected to 10% SDS-PAGE and phosphorylated Akt was determined by immunoblot analysis with an anti-phospho-Akt antibody. A western blot analysis with an anti-Akt antibody was performed to confirm that the same amounts of samples were used for the experiments. The results are shown FIG. 4. Results of FIG. 4 are the representative of 3 independent experiments.

It was observed that WKYMVm stimulation induced Akt phosphorylation in a time-dependent manner in FPR- and FPRL1-expressing RBL-2H3 cells (FIG. 4A). WKYMVm-induced Akt phosphorylation was sensitive to PTX, LY294002 but not to GFX and BAPTA/AM, indicating PTX-sensitive G-proteins(s) and PI3K-dependency (FIG. 4B). Stimulation of FPR-expressing RBL-2H3 cells not only with WKYMVm but also with the present peptides (WKGMVm (SEQ ID NO:1), WKRMVm (SEQ ID NO:11), WKYMVE (SEQ ID NO:16), and WKYMVR (SEQ ID NO:18)) caused Akt phosphorylation (FIG. 4C). WKYMVm and the present peptides also stimulated Akt phosphorylation in FPRL1-expressing RBL-2H3 cells (FIG. 4C). These results correlate with ERKs phosphorylation by the peptides in two types of cells (FIG. 3C). Since WKYMVm-induced ERKs and Akt activation were mediated by PI3K activation, it appears as if WKGMVm (SEQ ID NO:1), WKRMVm (SEQ ID NO:11), WKYMVE (SEQ ID NO:16), and WKYMVR (SEQ ID NO:18) successfully induce PI3K-mediated signaling in the downstream of FPR.

EXAMPLE 7

Effect of the Peptides on Exocytosis

Figure 5:
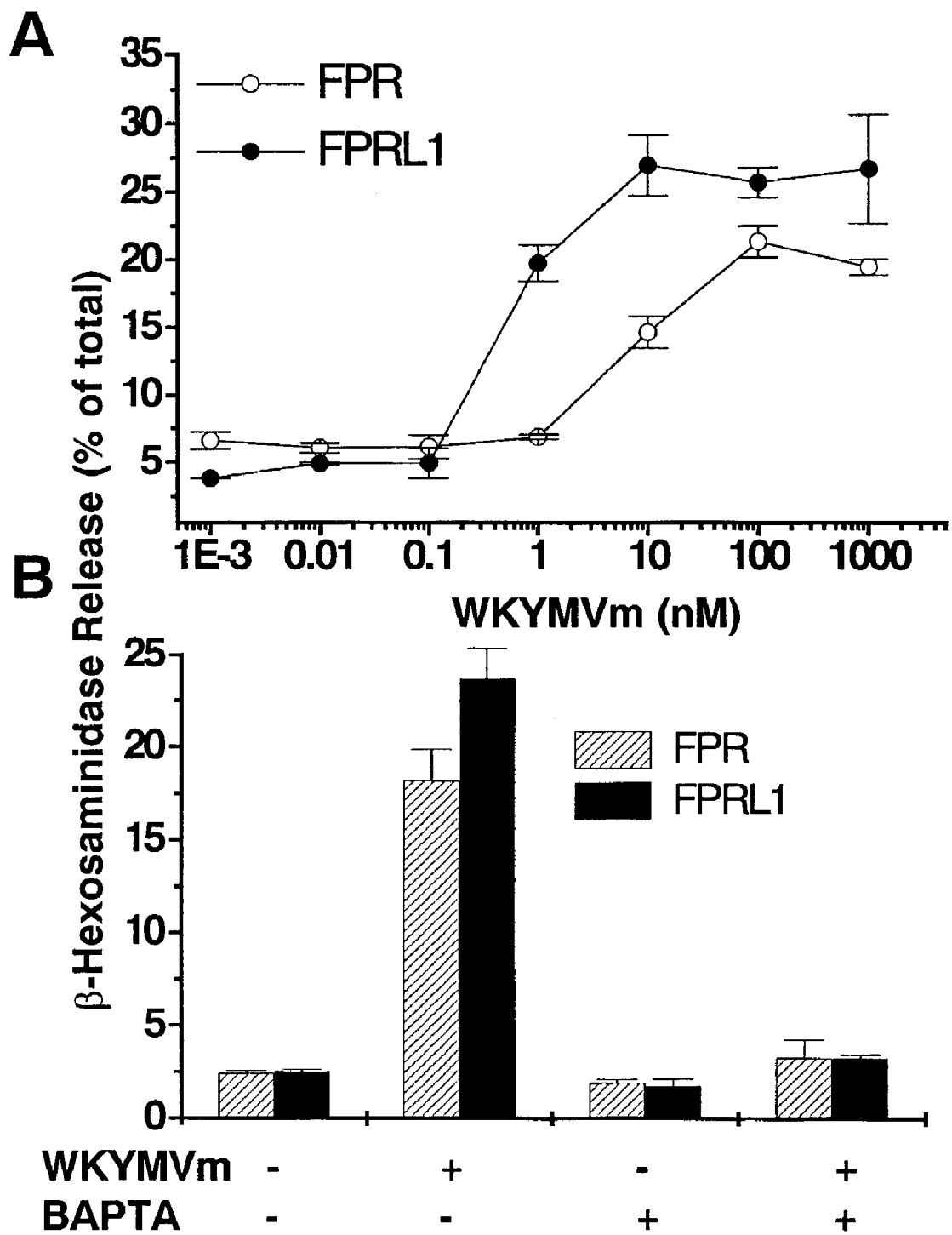
FIG. 5 shows WKYMVm which stimulates exocytosis in FPR- or FPRL1-expressing RBL-2H3 cells via intracellular calcium increase.

Granule secretion is one of the most important function of mast cells (20). The effect of WKYMVm on granule secretion was checked by measuring β-hexosaminidase secretion as described above. Haribabu, B., Zhelev, D. V., Pridgen, B. C., Richardson, R. M., Ali, H., and Snyderman, R. (1999) J. Biol. Chem. 274, 37087–37092. Briefly, RBL-2H3 cells ($2\times10^5$/well) expressing FPR or FPRL1 were cultured overnight in a 24-well tissue culture plate. The cells were washed twice with Tyrode's buffer (137 mM NaCl, 12 mM $NaHCO_3$, 5.6 mM glucose, 2.7 mM KCl, 1 mM $CaCl_2$, 0.5 mM $MgCl_2$, 0.4 mM $NaH_2PO_4$, 0.1 g/100 ml BSA, and 25 mM HEPES, pH 7.4) and stimulated with each peptide. Various concentrations of WKYMVm were treated in FPR- or FPRL1-expressing RBL-2H3 cells (FIG. 5A). 1 μM of WKYMVm was used to stimulate two cell lines in the absence or presence of 10 μM BAPTA/AM (FIG. 5B). The reaction was terminated 20 min after stimulation by placing the plate on ice. Secretion of β-hexosaminidase into the medium was determined by incubating 50 μl of supernatant or cell lysate with 25 μl of 0.5 mM p-nitrophenyl-N-acetyl-β-D-glucosamide in 0.1 M sodium citrate buffer (pH 3.8) at 37° C. for 2 hr. At the end of the incubation, 50 μl of 0.4 M $Na_2CO_3$ were added. Absorbance was monitored at 405 nm. The results are shown in FIG. 5. Data are means±S.E. of a single representative of three experiments performed in triplicate. Values (means±S.F.) were expressed as a percent of total β-hexosaminidase present in the cells.

Stimulation of FPR- or FPRL1-expressing RBL-2H3 cells with various concentrations of WKYMVm caused β-hexosaminidase release in a concentration-dependent manner (FIG. 5A). The maximal activity was shown with 100 nM or 10 nM peptide stimulation in FPR- or FPRL1-expressing RBL-2H3 cells, respectively (FIG. 5A). It has been reported that cytosolic calcium increase is critical for the secretion of granules in mast cells such as RBL-2H3. Haribabu, B., Zhelev, D. V., Pridgen, B. C., Richardson, R. M., Ali, H., and Snyderman, R. (1999) J. Biol. Chem. 274, 37087–37092; Jin, X., Shepherd, R. K., Duling, B. R., and Linden, J. (1997) J. Clin. Invest. 100, 2849–2857. It is also confirmed that chelation of intracellular calcium by BAPTA/AM treatment prior to the peptide stimulation almost completely inhibited WKYMVm-induced granule secretion (FIG. 5B).

Figure 6:
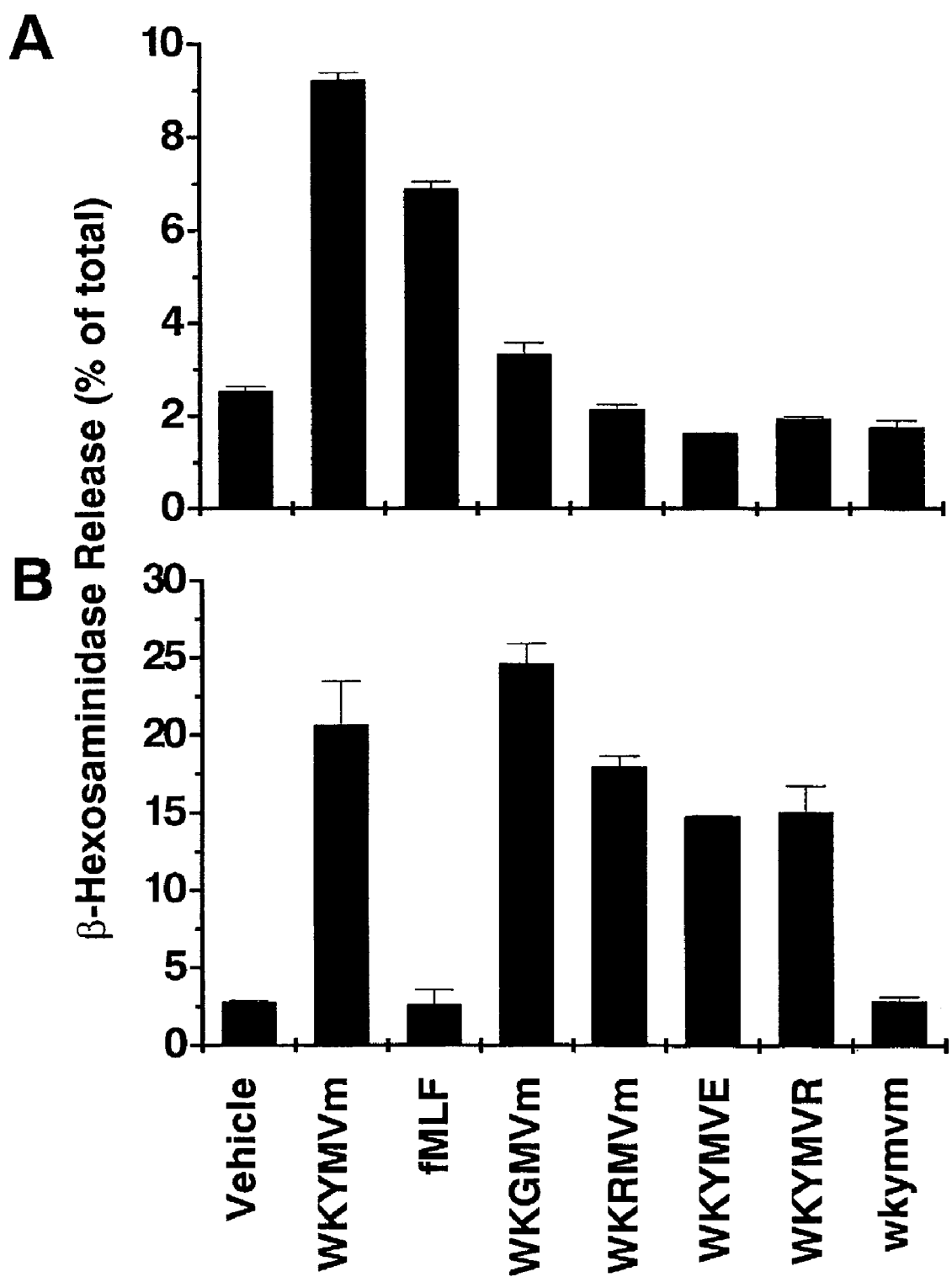
FIG. 6 shows the effect of WKYMVm, the peptides of the present invention (WKGMVm (SEQ ID NO:1), WKRMVm (SEQ ID NO:11), WKYMVE (SEQ ID NO:16), WKYMVR (SEQ ID NO:18)), fMLF, and wkymvm on exocytosis effects of N-formyl-methionyl-leucyl-phenylalanine (fMLF) on the peptide-induced $[Ca^{2+}]i$ increase.

From the new finding that cytosolic calcium release was induced by WKYMVm and many of the substituted peptides of WKYMVm but not by some of them (WKGMVm (SEQ ID NO:1), WKRMVm (SEQ ID NO:11), D-Met[6] substituted peptides), the effect of the peptides on granule secretion in RBL cells was checked. 10 μM of each peptide was treated in FPR- (FIG. 6A) or FPRL1-expressing RBL-2H3 cells (FIG. 6B). The peptide-induced secretion of β-hexosaminidase was determined as above. Data are means±S.E. of a single representative of three experiments performed in triplicate.

When FPR cells were stimulated with peptides (WKYMVm, WKGMVm (SEQ ID NO:1), WKRMVm (SEQ ID NO:11), WKYMVE (SEQ ID NO:16), WKYMVR (SEQ ID NO:18)), granule secretion was observed with some substituted peptides, except WKGMVm- (SEQ ID NO:1), WKRMVm- (SEQ ID NO:11), and D-Met$^6$-substituted peptides (FIG. 6A). The WKGMVm- (SEQ ID NO:1), WKRMVm- (SEQ ID NO:11), and D-Met$^6$ peptides could not effect granule secretion in FPR-expressing RBL-2H3 cells (FIG. 6A). These results absolutely correlate with the previous results that WKGMVm- (SEQ ID NO:1) WKRMVm- (SEQ ID NO:11) and D-Met6-substituted peptides could not induce cytosolic calcium release (FIG. 1A). Unlike in FPR-expressing RBL-2H3 cells, all the peptides (WKYMVm, WKGMVm (SEQ ID NO:1), WKRMVm (SEQ ID NO:11), WKYMVE (SEQ ID NO:16), WKYMVR (SEQ ID NO:18), but not fMLF or wkymvm, stimulated granule secretion in FPRL1-expressing RBL-2H3 cells (FIG. 6B). It is also perfectly correlated with the previous results that the peptides stimulated cytosolic calcium increase in FPRL1-expressing RBL-2H3 cells (FIG. 1B).

EXAMPLE 8

Effect of Peptides on Cellular Chemotaxis

Figure 7:
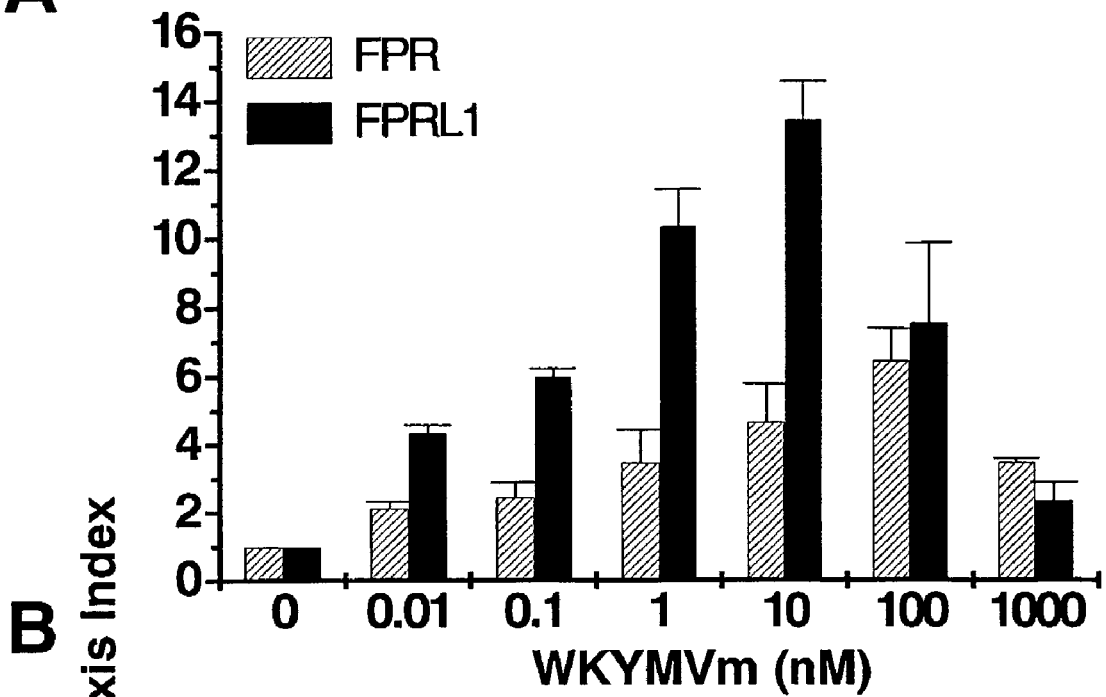
FIG. 7 shows WKYMVm which stimulates chemotactic migration of FPR- or FPRL1-expressing RBL-2H3 cells via P13K and MEK activity.
Figure 7:
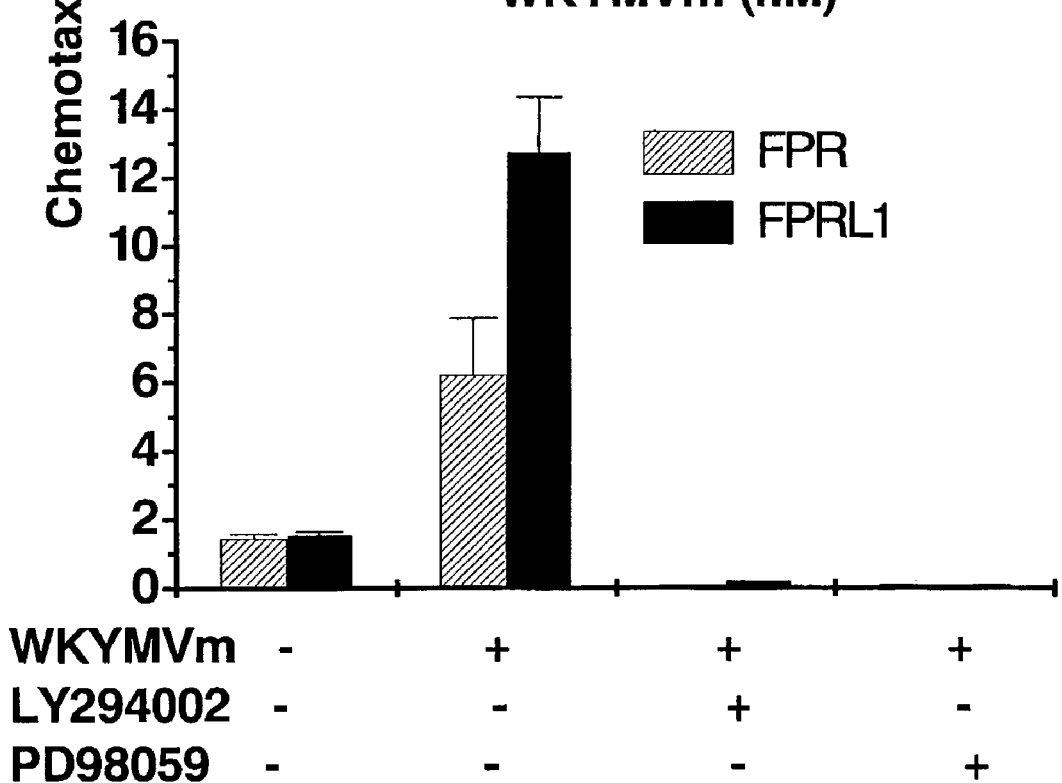

Chemotaxis assays were performed using multiwell chambers (modified Boyden chamber assay) (Neuroprobe Inc., Gaithersburg, Md.). Haribabu, B., Zhelev, D. V., Pridgen, B. C., Richardson, R. M., Ali, H., and Snyderman, R. (1999) J. Biol. Chem. 274, 37087–37092. Briefly, polycarbonate filters (8 μm pore size) were precoated with 50 μg/ml of rat type I collagen (Collaborative Biomedicals) in a HEPES-buffered RPMI 1640 medium. A dry coated filter was placed on a 96-well chamber containing different concentrations of peptides. RBL-2H3 cells expressing FPR or FPRL1 were suspended in RPMI at a concentration of 1×10$^6$ cells/ml of serum-free RPMI, and 25 μl of the suspension were placed onto the upper well of the 96-well chemotaxis chamber. After incubation for 4 hours at 37° C., non-migrated cells were removed by scraping them out, and cells that migrated across the filter were dehydrated, fixed, and stained with hematoxylin (Sigma, St. Louis, Mo.). The stained cells in five randomly chosen high power fields (HPF) (400×) in that well were then counted. FIG. 7A shows the results of the chemotaxis assay. The vehicle, 50 μM LY294002 (15 min), and 50 μM PD98059 (60 min) pretreated cells were subjected to the chemotaxis assay with 1 μM WKYMVm, and the results are shown in FIG. 7B. The numbers of migrated cells were determined by counting them in a high power field (400×). The Data are presented as means±SE of three independent experiments each performed in duplicate.

It has been reported that WKYMVm can induce chemotactic migration of phagocytic cells such as monocytes and neutrophils. Bae, Y. S., Kim, Y., Kim, Y., Kim, J. H., Suh, P. G., and Ryu, S. H. (1999) J. Leukoc. Biol. 66, 915–922. Le et al. demonstrated WKYMVm-induced cellular chemotaxis via binding to FPR and FPRL1. Le, Y., Gong, W., Li, B., Dunlop, N. M., Shen, W., Su, S. B., Ye, R. D., and Wang, J. M. (1999) J. Immunol. 163, 6777–6784. As expected, WKYMVm showed chemotactic migratory activity showing bell-shape concentration-dependency in FPR- or FPRL1-expressing RBL-2H3 cells (FIG. 7A). The WKYMVm-induced cellular chemotaxis was sensitive to LY294002 and PD98059 (FIG. 7B). The results suggest that WKYMVm-induced cellular chemotaxis is P13K- and MEK-dependent. WKYMVm stimulates chemotactic migration of FPR- or FPRL1-expressing RBL-2H3 cells via P13K and MEK activity.

The effect of the peptides of the present invention on cellular chemotaxis in FPR- or FPRL1-expressing RBL-2H3 cells was measured. Various concentrations of each peptide were used for the chemotaxis assay with FPR- or FPRL1-expressing RBL-2H3 cells. The numbers of migrated cells were determined by counting them in a high power field (400×). The Data are presented as means SE of two independent experiments each performed in duplicates.

Figure 8:
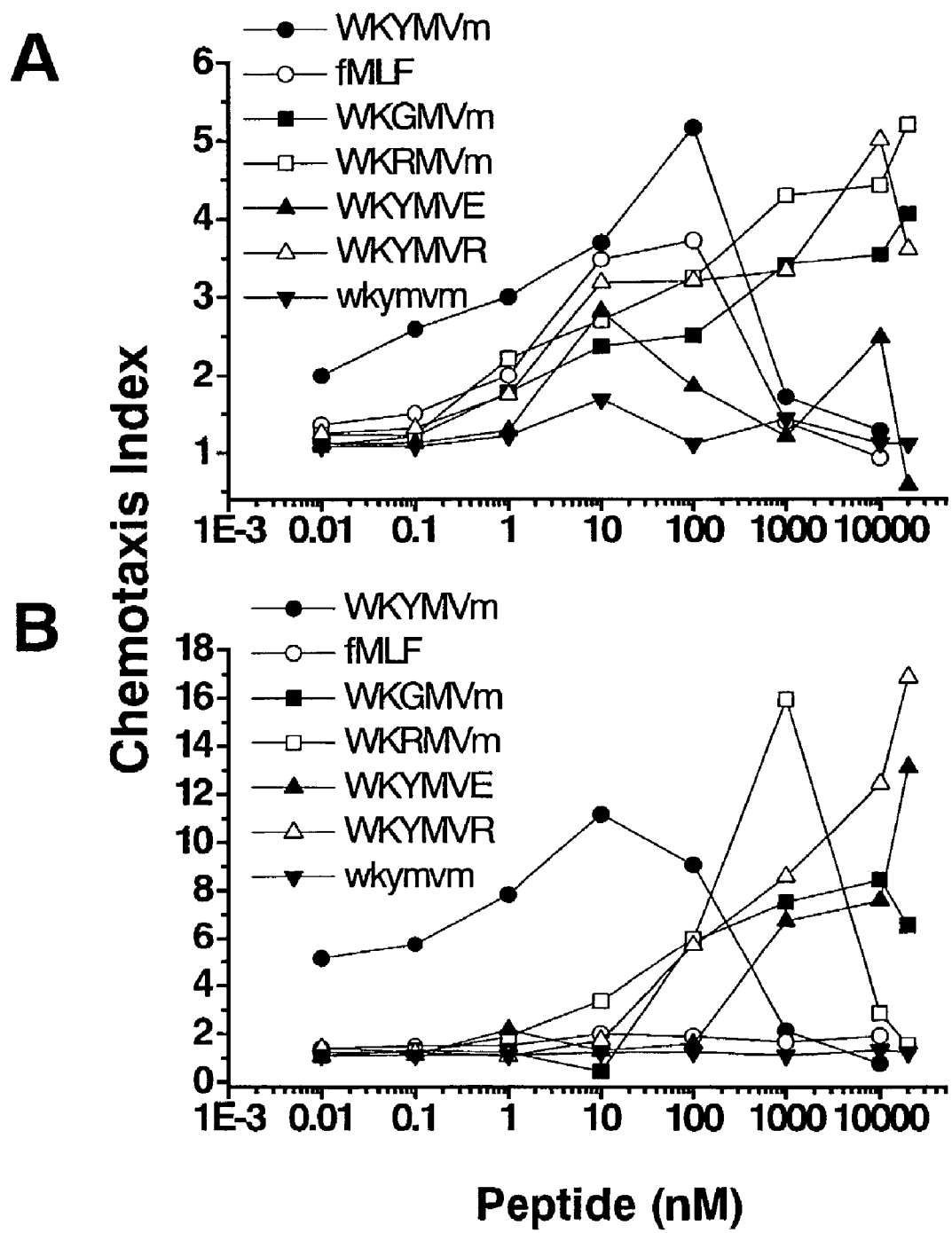
FIG. 8 shows the effect of WKYMVm, the peptides of the present invention (WKGMVm (SEQ ID NO:1), WKRMVm (SEQ ID NO:11), WKYMVE (SEQ ID NO:16), WKYMVR (SEQ ID NO:18)), fMLF, and wkymvm on chemotaxis.

In FPR-expressing RBL-2H3 cells, not only WKYMVm, but also the substituted peptides (WKGMVm (SEQ ID NO:1), WKRMVm (SEQ ID NO:11), WKYMVE (SEQ ID NO:16), and WKYMVR (SEQ ID NO:18)) induced cellular chemotaxis (FIG. 8A). The concentrations needed for chemotaxis by the substituted peptides are higher than by WKYMVm (FIG. 8B). On the signaling pathways involved in substituted peptides-induced chemotaxis, the involvement of PI-3 kinase and MEK-mediated signaling was tested. When FPR-expressing RBL cells were pretreated with LY294002 or PD98059, the WKYMVm and the substituted peptides-induced RBL cell migration was almost completely inhibited (FIG. 7B and data not shown). In FPRL1-expressing RBL-2H3 cells, WKYMVm and the peptides (WKGMVm (SEQ ID NO:1), WKRMVm (SEQ ID NO:11), WKYMVE (SEQ ID NO:16), and WKYMVR (SEQ ID NO:18)) also induced cellular chemotaxis showing concentration-dependency (FIG. 8B).

In the present invention, it is demonstrated that FPR can be modulated by distinct ligands leading to differential cellular signaling and functional consequences, for the first time. To demonstrate the ligand-specific modulation of FPR, the diverse peptides, a potent ligand for FPR were generated as listed in Table I. Among the peptides, WKGMVm- (SEQ ID NO:1), WKRMVm- (SEQ ID NO:11), and D-Met$^6$-substituted peptides bind to FPR, just inducing PI-3 kinase-mediated Akt and MEK-mediated ERK activation resulting in chemotactic migration of the cells. These peptides could not effect a cytosolic calcium increase. Since the peptide WKYMVm stimulates not only ERKs activation but also cytosolic calcium increase leading to chemotaxis and degranulation, it can be suggested that FPR can be differentially modulated by distinct ligands.

Recently, several reports have demonstrated that some GPCRs could be modulated by distinct ligands. Thomas, W. G., Qian, H., Chang, C. S., and Karnik, S. (2000) J. Biol. Chem. 275, 2893–2900; Palanche, T., Ilien, B., Zoffmann, S., Reck, M. P., Bucher, B., Edelstein, S. J., and Galzi, J. L. (2001) J. Biol. Chem. 276, 34853–34861. In the process of ligand-specific modulation of GPCR, a different ligand has been suggested to induce distinct conformational change of the receptor and induce selective coupling of the receptor with certain effector molecules or G-proteins. In Table III and FIG. 1A, it is demonstrated that that WKGMVm (SEQ ID NO:1), WKRMVm (SEQ ID NO:11), and D-Met$^6$ substituted peptides could not stimulate a PLC-mediated cytosolic calcium increase in FPR-expressing RBL-2H3 cells. However, these peptides stimulated ERKs and Akt phosphorylation in FPR-expressing RBL-2H3 cells (FIG. 3C). In the WKYMVm and the present peptide-mediated cell signaling, a cytosolic calcium increase is induced by the hydrolysis of PI through PLC-β activation, but ERK and Akt phosphorylation is mediated by the activation of MEK and PI3 kinase, respectively. Keeping in mind these results, it appears as if binding of a peptide ligand to FPR induces a conformational change of FPR, and the conformation change offers the coupling of the receptor with G-protein-mediated PLC-β or G-protein-mediated PI-3 kinase. Since some of the present peptides that could not induce a cytosolic calcium increase (WKGMVm (SEQ ID NO:1), WKRMVm (SEQ ID NO:11), and D-Met$^6$ substituted peptides) could stimulate ERKs phosphorylation via the PI-3 kinase-dependent pathway, it appears as if the peptides bind to FPR and induce a conformational change needed for the activation of PI-3 kinase and MEK-mediated signaling, resulting in chemotactic migration of RBL-2H3 cells.

Two different receptors of the formyl peptide receptor family, FPR and FPRL1, have been reported to serve important roles in innate immune responses. Le, Y., Li, B., Gong, W., Shen, W., Hu, J., Dunlop, N. M., Oppenheim, J. J., and Wang, J. M. (2000) Immunol Rev. 177, 185–194.; Le, Y., Oppenheim, J. J., and Wang, J. M. (2001) Cytokine Growth Factor Rev. 12, 91–105. Until now, several different ligand origins including the formyl peptide lipoxin A4 have been reported to bind FPR or FPRL1. Le et al. reported that WKYMVm could bind to FPR and FPRL1. 12. Le, Y., Gong, W., Li, B., Dunlop, N. M., Shen, W., Su, S. B., Ye, R. D., and Wang, J. M. (1999) J. Immunol. 163, 6777–6784.

In the present invention, the inventor demonstrated that substitution of Tyr$^3$ or D-Met$^6$ with other amino acids abolished PLC-mediated cytosolic calcium-increasing activity of FPR but not of FPRL1 (FIG. 1). This result indicates that Tyr$^3$ and D-Met$^6$ are critical for the activation of PLC by FPR but not by FPRL1. From this result it can be deduced that the ligand-binding site of FPR and FPRL1 will be different.

GPCRs including FPR induce intracellular signaling via binding to hetero-trimeric G-proteins(s), and many research groups have tried to reveal the critical amino acid residues of receptors involved in G-protein coupling. Prossnitz, E. R., Quehenberger, O., Cochrane, C. G., and Ye, R. D. (1993) Biochem. J. 294, 58 1–587; Miettinen, H. M., Gripentrog, J. M., Mason, M. M., and Jesaitis, A. J. (1999) J Biol. Chem. 274, 27934–27942. In FPR, Miettinen et al. constructed 35 mutant FPRs and checked the effect of mutation on G-protein coupling and cellular signaling of FPR. According to the paper, S63, D71, R123, and C124/C126 are important for G-protein coupling to FPR. Among the mutants, the R123A mutant that was unable to mediate calcium mobilization could induce ERKs phosphorylation by fMLF. It has been also postulated that Asp122 and Arg123, which form the conserved (D/E)RY motif (DRC in FPR), participate in a hydrogen bonding network that stabilizes the inactive form of the receptor. In the postulation, a ligand binding to a receptor causes alteration of the hydrogen-bonding network, and certain amino acid residues, for example arginine in the DRY motif, become exposed to enable interaction with G-protein. It was found that some peptides such as WKGMVm (SEQ ID NO:1) could induce ERKs phosphorylation but not calcium mobilization. It will be important to determine whether ligation of WKYMVm or WKGMVm (SEQ ID NO:1) to FPR induces a differential conformational change of the receptor; i.e. although WKYMVm can induce a conformational change of FPR including alteration of the hydrogen bonding of the DRY motif, WKGMVm (SEQ ID NO:1) just causes a distinct conformation change of the receptor without affecting DRY hydrogen bonding. In the case of FPRL1, it also contains the DRY motif (DRC in FPRL1), but its role in G-protein coupling has not been checked. In the results, not only WKYMVm but also WKGMVm (SEQ ID NO:1) induced calcium mobilization in FPRL1-expressing RBL cells (FIG. 1B). These results suggest that WKYMVm or WKGMVm (SEQ ID NO:1) do not affect hydrogen bonding of the DRY motif in FPR or FPRL1. Other binding pockets would be involved for the peptide binding, and as a further work it will be important to identify the residues involving in the differential binding pattern for WDYMVm or WKGMVm (SEQ ID NO:1) to FPR.

Until now, it has not been reported that certain natural ligands could modulate FPR differentially. In immune systems, differential regulation of degranulation or chemotactic migration will be required for more defined regulation. In view of this, it is important to identify ligands that modulate FPR differentially, as in the present invention.

What is claimed is:

1. A peptide comprising the amino acid sequence SEQ ID NO: 1.

2. The peptide according to claim 1 wherein the peptide activates leukocytes and is in an isolated and substantially pure form.

3. The peptide according to claim 1 wherein the peptide has at least one of the following properties:
   (a) inducing superoxide generation by human monocytes or neutrophils;
   (b) inducing an intracellular calcium increase by human peripheral blood monocytes or neutrophils;
   (c) binding to formyl peptide receptor or formyl peptide receptor-like 1;
   (d) inducing chemotactic migration of human monocytes or neutrophils in vitro;
   (e) inducing degranulation in formyl peptide receptor expressing cells or formyl peptide receptor-like 1 expressing cells;
   (f) stimulating extracellular signal-regulated protein kinase phosphorylation via activation of formyl peptide receptor or formyl peptide receptor-like 1; and
   (g) stimulating Akt phosphorylation via activation of formyl peptide receptor or formyl peptide receptor-like 1.

4. A pharmaceutical composition comprising a peptide of which its amino acid sequence is SEQ ID NO: 1.

5. A method of treating a condition accompanied or caused by modification of the number or activation states of leukocytes comprising administering to a host in need of such treatment a therapeutically effective amount of peptides having an amino acid sequence of SEQ ID NO: 1.

6. The method according to claim 5 wherein the condition is bacterial, mycoplasma, yeast, fungal, or viral infection.

7. The method according to claim 5 wherein the condition is an inflammation.

8. A method of increasing the number or raising the activation state of leukocytes in a host comprising administering to a host in need of a greater number or higher activation state of leukocytes a therapeutically effective amount of peptides having an amino acid sequence SEQ ID NO: 1.

9. A method of inducing extracellular calcium increase in leukocytes in a patient in need of such treatment, the method comprising administering to said patient an amount of a peptide having an amino acid sequence of SEQ ID NO: 1 in an amount effective to therapeutically or prophylactically achieve induction or desensitization.

10. A method of inducing superoxide generation by human monocytes or neutrophils in a patient in need of such treatment, the method comprising administering to said patient an amount of a peptide having an amino acid sequence of SEQ ID NO: 1 in an amount effective to therapeutically or prophylactically achieve induction or desensitization.

11. A method of inducing chemotactic migration by human peripheral blood mononuclear cells in a patient in need of such treatment, the method comprising administering to said patient an amount of a peptide having an amino acid sequence of SEQ ID NO: 1 in an amount effective to therapeutically or prophylactically achieve induction or desensitization.

12. A method of inducing degranulation in formyl peptide receptor or formyl peptide receptor-like 1 expressing cells in a patient in need of such treatment, the method comprising administering to said patient an amount of a peptide having an amino acid sequence of SEQ ID NO: 1 in an amount effective to therapeutically or prophylactically achieve induction or desensitization.

13. A method of inhibiting binding of WKYMVm to a formyl peptide receptor in the formyl peptide receptor expressing cells, in a patient in need of such treatment, the method comprising administering to said patient an amount of a peptide having an amino acid sequence of SEQ ID NO: 1 in an amount effective to therapeutically or prophylactically achieve inhibition.

14. A method of inhibiting binding of WKYMVm to a formyl peptide receptor-like 1 in the formyl peptide receptor-like 1 expressing cells, in a patient in need of such treatment, the method comprising administering to said patient an amount of a peptide having an amino acid sequence of SEQ ID NO: 1 in an amount effective to therapeutically or prophylactically achieve inhibition.

15. A method of stimulating extracellular signal regulated protein kinase in formyl peptide receptor or formyl peptide receptor-like 1 expressing cells in a patient in need of such treatment, the method comprising administering to said patient an amount of a peptide having an amino acid sequence of SEQ ID NO: 1 in an amount effective to therapeutically or prophylactically achieve stimulation.

16. A method of stimulating Akt in formyl peptide receptor or formyl peptide receptor-like 1 expressing cells in a patient in need of such treatment, the method comprising administering to said patient an amount of a peptide having an amino acid sequence of SEQ ID NO: 1 in an amount effective to therapeutically or prophylactically achieve stimulation.

17. The method according to claim 5 wherein said host is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

18. The method according to claim 8 wherein said host is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

19. The method according to claim 9 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

20. The method according to claim 10 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

21. The method according to claim 11 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

22. The method according to claim 12 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

23. The method according to claim 13 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

24. The method according to claim 14 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

25. The method according to claim 15 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

26. The method according to claim 16 wherein said patient is afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, post-surgical inflammation, organ transplantation, or alopecia.

* * * * *